US005891720A

United States Patent [19]

Moore et al.

[11] Patent Number: 5,891,720
[45] Date of Patent: Apr. 6, 1999

[54] ISOLATED DNA ENCODING A NOVEL HUMAN G-PROTEIN COUPLED RECEPTOR

[75] Inventors: Karen Moore, Maynard; Deborah Lynn Nagle, Watertown; Elizabeth A. Woolf, Georgetown, all of Mass.

[73] Assignee: Millennium Pharmaceuticals, Inc., Cambridge, Mass.

[21] Appl. No.: 833,226

[22] Filed: Apr. 17, 1997

[51] Int. Cl.$^6$ .......................... C12N 15/85; C12N 15/63; C07H 21/04; C12Q 1/68
[52] U.S. Cl. ........................... 435/325; 435/6; 435/320.1; 435/366; 536/23.1; 536/23.5
[58] Field of Search .......................... 435/6, 320.1, 325, 435/366; 536/23.1, 23.5

[56] References Cited

FOREIGN PATENT DOCUMENTS

WO92/01810  2/1992  WIPO.
WO96/30406  10/1996  WIPO.

OTHER PUBLICATIONS

Niblett, D., GenBank, accession number Z84474 Mar. 7, 1997.
Bronstein, I. et al., 1994, "Chemiluminescent Reporter Gene Assays: Sensitive Detection of the GUS and SEAP Gene Products", Biotechniques 17:172–177.
Dray, A., 1995, "Inflammatory Mediators of Pain", Br. J. Anaesth. (England) 75(2):125–131.
Frankish, H.M. et al., 1995, "Neuropeptide Y, the Hypothalamus, and Diabetes: Insights Into the Central Control of Metabolism", Peptides 16(4):757–771.
Heilig, M. & Wilderlov, E., 1995, "Neurobiology and Clinical Aspects of Neuropeptide Y", Crit. Rev. Neurobiol. 9(2–3):115–136.
Kaye, W.H., 1996, "Neuropeptide Abnormalities in Anorexia Nervosa", Psychiat. Res. (Ireland) 62(1):65–74.
Leibowitz, S.F., 1995, "Brain Peptides and Obesity: Pharmacologic Treatment", Obes. Res. 3(4) Suppl.:573S–589S.
McConnell, H.M. et al., 1992, "The Cytosensor Microphysiometer: Biological Applications of Silicon Technology", Science 257:1906–1912.

Michel, M.C. & Rascher, W., 1995, "Neuropeptide Y: a Possible Role in Hypertension", J. Hypertens. (England) 13(4):385–395.
Parce, J.W. et al., 1989, "Detection of Cell–Affecting Agents with a Silicon Biosensor", Science 246:243–247.
Richard, D., 1995 "Exercise and the Neurobiological Control of Food Intake and Energy Expenditure", Int. J. Obesity Related Metab. Disord. (England) 19(4):S73–S79.
Rogers, D.F., 1995, "Neurokinin Receptors Subserving Airways Secretion", Can. J. Physiol. Pharmacol. (Canada) 73(7):932–939.
Strader, C.D. et al., 1994, "Structure and Function of G Protein–Coupled Receptors", Annu. Rev. Biochem. 63:101–132.
Tian et al., 1996, "Structural Motifs Encoded by Individual Exons of the Human Neurokinin–1 Receptor Gene Interact Differentially with Selective Agonists and Antagonists", J. Neurochemistry 67:1191–1199.
Wettstein, J.G. et al., 1995, "Central Nervous System Pharmacology of Neuropeptide Y", Pharmacol. Ther. (England) 65(3):397–414.
Zukowska–Grojec, Z., 1995, "Neuropeptide Y: A Novel Sympathetic Stress Hormone and More", Ann. NY Acad. Sci. 771:219–233.

*Primary Examiner*—Nancy J. Degen
*Assistant Examiner*—Andrew Wang
*Attorney, Agent, or Firm*—Pennie & Edmonds, LLP

[57] ABSTRACT

The present invention relates to the discovery, identification and characterization of nucleic acids that encode a novel G protein coupled receptor (I5E) protein. The invention encompasses I5E nucleotides, host cell expression systems, I5E proteins, fusion proteins, polypeptides and peptides, antibodies to the receptor, transgenic animals that express an I5E transgene, or recombinant knock-out animals that do not express the I5E, antagonists and agonists of the receptor, and other compounds that modulate I5E gene expression or I5E activity that can be used for diagnosis, drug screening, clinical trial monitoring, and/or used to treat disorders such as inflammatory, central nervous system or gastrointestinal disorders.

16 Claims, 5 Drawing Sheets

```
AGCCGCAGAGCGCACAGAAAGGAGGCGCCGAGACAGACATCACC ATG GCA GCC CAG AAT GGA AAC ACC     8
                                              M   A   A   Q   N   G   N   T     68

S   F   T   P   N   F   N   P   P   Q   D   H   A   S   L   S   F   N   F     28
AGT TTC ACA CCC AAC TTT AAT CCA CCC CAA GAC CAT GCC TCC CTC TCC TTT AAC TTC    128

S   Y   G   D   Y   D   L   P   M   D   E   D   M   T   K   T   R   T         48
AGT TAT GGT GAT TAT GAC CTC CCT ATG GAT GAG GAC ATG ACC AAG ACC CGG CAA        188

F   F   A   A   K   I   V   I   G   I   A   L   A   G   I   M   L   V   C   G   68
TTC TTC GCA GCG AAG ATC GTC ATT GGC ATT GCA CTG GCA GGC ATC ATG CTG GTC GGC   248

I   G   N   F   V   F   I   A   A   N   L   R   Y   K   K   L   R   N   L   T     88
ATC GGT AAC TTT GTC TTT ATC GCT GCC AAC CTG CGC TAT AAG AAG CTG CGC AAC CTC ACC   308

N   L   L   I   A   I   A   I   S   D   F   L   V   A   I   C   C   L   P   108
AAT CTG CTC ATT GCC ATC GCC ATC TCC GAC TTC CTG GTG GCC ATC TGC TGC CCC       368

F   E   M   D   Y   Y   V   V   R   Q   L   S   W   E   H   G   H   V   L   C   128
TTC GAG ATG GAC TAC TAC GTG GTA CGG CAG CTC TCC TGG GAG CAT GGC CAC GTG CTC TGT   428

A   S   V   N   Y   L   R   T   V   S   L   Y   V   S   T   N   A   L   L   A   148
GCC TCC GTC AAC TAC CTG CGC ACC GTC TCC CTC TAC GTC TCC ACC AAT GCC TTG CTG GCC   488

I   A   I   D   R   Y   L   A   I   V   H   P   L   K   P   R   M   N   Y   Q   168
ATT GCC ATT GAC AGA TAT CTC GCC ATC GTT CAC CCC TTG AAA CCA CGG ATG AAT TAT CAA   548

T   A   S   F   L   L   I   L   A   L   V   W   M   V   S   I   L   I   A   P   S   188
ACG GCC TCC TTC CTG ATC CTG GCC TTG GTC TGG ATG GTG TCC ATT CTC ATT GCC ATC CCA TCG   608
```

FIG.1A

| A | Y | F | A | T | E | T | V | L | F | I | V | K | S | Q | E | K | I | F | C | 208 |
|---|---|---|---|---|---|---|---|---|---|---|---|---|---|---|---|---|---|---|---|---|
| GCT | TAC | TTT | GCA | ACA | GAA | ACC | GTC | CTC | TTT | ATT | GTC | AAG | AGC | CAG | GAG | AAG | ATC | TTC | TGT | 668 |

| G | Q | I | W | P | V | D | Q | Q | L | Y | Y | K | S | Y | F | L | F | I | F | 228 |
|---|---|---|---|---|---|---|---|---|---|---|---|---|---|---|---|---|---|---|---|---|
| GGC | CAG | ATC | TGG | CCT | GTG | GAT | CAG | CAG | CTC | TAC | TAC | AAG | TCC | TAC | TTC | CTC | TTC | ATC | TTT | 728 |

| G | V | E | F | V | G | P | V | T | M | T | L | C | Y | A | R | I | S | R | 248 |
|---|---|---|---|---|---|---|---|---|---|---|---|---|---|---|---|---|---|---|---|---|
| GGT | GTC | GAG | TTC | GTG | GGC | CCT | GTC | ACC | ATG | ACC | CTG | TGC | TAT | GCC | AGG | ATC | TCC | CGG | | 788 |

| E | L | W | F | K | A | V | P | G | F | Q | T | E | Q | I | R | K | R | L | R | 268 |
|---|---|---|---|---|---|---|---|---|---|---|---|---|---|---|---|---|---|---|---|---|
| GAG | CTC | TGG | TTC | AAC | GCA | GTC | CCT | GGG | TTC | CAG | ACG | GAG | CAG | ATT | CGC | AAG | CGG | CTG | CGC | 848 |

| C | R | R | K | T | V | L | M | C | L | I | T | A | Y | V | L | C | W | 288 |
|---|---|---|---|---|---|---|---|---|---|---|---|---|---|---|---|---|---|---|---|---|
| TGC | CGC | AGG | AAG | ACG | GTC | CTG | ATG | TGC | CTC | ATG | ATT | CTC | ACG | GCC | TAT | GTG | CTG | TGC | TGG | 908 |

| A | P | Y | G | F | T | I | R | D | F | F | P | T | V | F | V | K | E | 308 |
|---|---|---|---|---|---|---|---|---|---|---|---|---|---|---|---|---|---|---|---|---|
| GCA | CCC | TAC | GGT | TTC | ACC | ATC | CGT | GAC | TTC | TTC | CCC | ACT | GTG | TTC | GTG | AAG | GAA | | | 968 |

| K | H | Y | L | T | A | F | Y | V | V | E | C | I | A | M | S | N | S | M | I | 328 |
|---|---|---|---|---|---|---|---|---|---|---|---|---|---|---|---|---|---|---|---|---|
| AAG | CAC | TAC | CTC | ACT | GCC | TTC | TAC | GTC | GTG | GAG | TGC | ATC | GCC | ATG | AGC | AAC | AGC | ATG | ATC | 1028 |

| N | T | V | F | R | P | S | Q | K | R | G | S | K | S | S | Y | F | K | M | M | 348 |
|---|---|---|---|---|---|---|---|---|---|---|---|---|---|---|---|---|---|---|---|---|
| AAC | ACC | GTG | TTC | CGT | CCC | TCC | CAG | AAG | CGG | GGG | AGC | AAG | TCC | AGT | TAC | TTC | AAG | ATG | ATG | 1088 |

| L | L | H | W | R | P | S | Q | K | S | A | D | L | R | 368 |
|---|---|---|---|---|---|---|---|---|---|---|---|---|---|---|---|---|---|---|---|---|
| CTG | CTG | CAC | TGG | CGT | CCC | TCC | CAG | AAG | TCC | AGT | GCT | GAC | CTT | AGA | | | | | | 1148 |

| T | N | G | V | P | T | T | E | E | V | D | C | I | R | L | K | * | 385 |
|---|---|---|---|---|---|---|---|---|---|---|---|---|---|---|---|---|---|

FIG. 1B

```
ACC AAC GGG GTG CCC ACC ACA GAA GAA GTG GAC TGT ATC AGG CTG AAG TGA                1199
CCCACTGGTGTCACACAATTGAAAACCCCAGTCCAGTACTCAGAGCATCACCCACCATCAACCAAGTTCATAGGCTGCA    1278
TGGGAAATGACATCTGTGTTCATGCCTCCCCGTGCCCTCAAGAAGCCGAATGCTGCAAAGTCGTAACATACAATGAGA     1357
CTAGACATGAACCAAATCAGCTGACATTTACTGATATCCGCTCTGACACCTACTGTGTCCACAATCCCCACAAGGAGATT   1436
AGACACAAGGAGCAGCAACTGACATGGACTGAACATGTACTGTGTGCAAACCACCACCAATGAGATTAGACGGGACAGC    1515
AGGAGCTGACATTTACTCTTCACCTACTGTAATCAAAACACTTGATTGATTACAATCAAAAACATATAAAAAAACATA    1594
ACAAAGTAGCAGAAGCTATTGGAGTTTCCAAGCTATCTCCAGATATATAGATAGTTCACCTCCATCTTCCCTAATTCT     1673
GTATCTTACCAGTGCAGGATCACTTGAGGTCAGGAGTTCAACCCAGGCTGGCCAACATGGTGAAACCCTGTCTCTAAAA    1752
GGCTGAGGCACGTGGATCACTTGAGGTCAGGAGTTCAACCCAGGCTGGCCAACATGGTGAAACCCTGTCTCTACTAAAA    1831
ATACAAAATTAGCCGTGGTGGTGGCGGGCGCCTGTAATCCCAGTTACTCAGGAGGCTGAAGCAGGAGAATAGCTTGAA     1910
CCTGGGAGTTGGAGTTTGCAGTGAGCTGAGATTGCTCCACTGCACTCCAGCCTGACTCGAGTGACAGAGTGAGACTCTGTCTCA 1989
GGAAAAAAACAAACAAACAAACAAACAAACAAACAAACAAACAAACAACCAACGGCTATAGAAGAGACTGTTAGAC        2068
ACAATGGAAATGTAACGATAAGTTTGTCAGTGCGTGGTTTACAGCATCATGGGAGGTGCGTTACAGCCATCATACTGAA    2147
CTTTCCCACCCACCTCCTACTGCCTCCCAGGGCATTCTCTAGGATTTGGCTTCAAGAAAAAAATTCTTATAGTCA        2226
GCCCAGCCTTATGTGGTTATCCACAATGGTGTAATTTCAAAGGAAAGAACCTAAAAATCACTTTCCCACTGATGCTTGA    2305
AAGCTTATCATTTTATTTGGGTGGAGATGGGTAATCCTGAGGTGTCAATTTTTGCCTCCTCAGTGCAAAGGATTTCAGT    2384
```

FIG. 1C

```
GGCTCTGGGGTCAGGGGGAAAGAGGACAGAGAAAAAGTGGAGGTTGCCACTGGCAATGAACATAATCTCTGTGGGCAT      2463

TTTGCTAAGGACTGGACCACTTTCTAGAACACTCCCTCTTTTACAAAGGAACTCTACCTAGAATCCAAAGACCTGGGT      2542

TCAGGTCCTAACTCTAAGACTCAAGTCCTAAATTCATGATGTTTCTCTCTGTGTCTCACTTTTGCTTAATGAAATGG      2621

CGATGATGAAATATCTGCTCTTCATACCTTGCAAGACTGTGGGAGAGCCCATTGAGGCCATGGTTGTGAATGTGCT      2700

TTTCAACTGTGCACACGATAAGAATGGAGAAGTGATATTGAACAGTTTATTTGGAGGGAGTTTATTTGGAAACCCCATC      2779

CACTGTGATTTATTAGAGAAATACCCCACACTTTTCATCCTGTTCTTTGGATGAAAGACTCCTGAAGACTTCACAGTG      2858

TACCTTGTCTACAGTGGGCCAAAAAGGGATCCCTGTTCTTGGTTATAATCTGGGAAATTTAACCTCAGATTCTCAGTGA      2937

CCCCAAGACTCTCAGCATCCCTGCGGTCTTAGAAGTGTGTATTATTATACATTGTGTAACTGTAGGTACACGTCTTCATTCTTCTT      3016

TGCATAAATATCACTTCTGAATCTGTTTGTATTATGCAAATGGTACCTGGTTTGGGACTGACCCATCCATATTTGACCAATTCCTAATTT      3095

GATTCATTTGATGTGTAGCTATGCAAATGGTACCTGGTTTGGGACTGACCCATCCATATTTGACCAATTCCTAATTT      3174

TTTATAGACAAGGAATTAATTGTTTGCTTGTTTGATTGTTTCTATTATTTGATTTGTTGTGTGACTGAAGTTTCA      3253

ACCAATGTTTCTTTCTATCACCACCCAGCAGACTCACCTTCAGCCCAATCATTGTACTCTCAGAAAAATGCAGGCCGGCA      3332

TGGTGGCTCACATCTGTAATCCCAGCACTTCGGGAGGCCAAGATGGGCAGATCACCTGAGGTCAGGAGTTCAAGACCAG      3411
```

FIG.1D

| Sequence | Position |
|---|---|
| CCTGGCCAACATGGCAAACCCCATCTCTAGAAAATACAGAAATTAGCTGGGCGTGGTGGCACATGCCTGTGGTCCCAG | 3490 |
| CTCCTCAGGAGGCTGAGGCATGAGAATTGCTTGAACCCCAGAGGCAGAGGTTGCAGTGAATTGAGATCGCCACCACTGCA | 3569 |
| CTCCAGCCTGGGTGATAGAGCAAGATTCCATCTCAAAGGAAAATAAAAGAGAAAATGCAAACACACTATAATATTAGCCT | 3648 |
| AAGCAAAAACTGTTAATTCTGATTTACAAAAATTCTTACTTGCTTGGCTTTGAAATGCATTGTGTAATAATGCATTTCAA | 3727 |
| AGCCAAGCAAGTAACAATTTTAGGTTATGTACATTTCTATAAATATAATTGTATTTTATTTATTATTCTATCCTG | 3806 |
| GCTGTTAGCCGAATCAGGAGATTCTTTAGGAATGGACCATGTACCAGTCAAGTCTGTCAGCAGGATTCATCACCCTGTT | 3885 |
| CCTTTTGTCCTAGAATATACCAACTTCCTTTCATTGAAATTTAACTGAAAAAACTTTTGTAAATATCAGTGTGTATTT | 3964 |
| GTGATTTTCCAGTGATTAAAGTGTGATGTTGTTATCCAATTAAATAATTAACATGTGGAATTTAAAAAAAAAAAAAAG | 4043 |
| GGCGGCCGC | 4052 |

FIG.1E

ISOLATED DNA ENCODING A NOVEL HUMAN G-PROTEIN COUPLED RECEPTOR

1. INTRODUCTION

The present invention relates to the discovery, identification and characterization of nucleic acids that encode a novel G protein coupled receptor (referred to herein as I5E). The invention encompasses I5E nucleotides, host cell expression systems, I5E proteins, fusion proteins, polypeptides and peptides, antibodies to the receptor, transgenic animals that express a I5E transgene, or recombinant knock-out animals that do not express the I5E, antagonists and agonists of the receptor, and other compounds that modulate I5E gene expression or I5E activity that can be used for diagnosis, drug screening, clinical trial monitoring, and/or used to treat disorders such as inflammatory, central nervous system or metabolic disorders such as body weight disorders including obesity, cachexia and anorexia.

2. BACKGROUND OF THE INVENTION

Many biological processes are mediated by proteins participating in signal transduction pathways that involve G-proteins and/or second messengers. G-protein coupled receptors are plasma membrane proteins capable of transducing signals across a cell membrane so as to initiate a second messenger response. To this end, the G-protein coupled receptors bind a variety of ligands ranging from small biogenic amines to peptides, small proteins and large glycoproteins (C. D. Strader et al., Annu. Rev. Biochem. 63, 101–132 (1994)). All G-protein coupled receptors have been characterized as having seven hydrophobic domains, which have been postulated to span the plasma membrane, connected by hydrophilic extracellular and intracellular loops. The G-protein family of coupled receptors includes dopamine, calcitonin, adrenergic, endothelin, CAMP, adenosine, serotonin, follicle stimulating hormone, opsin and rhodopsin receptors.

G-protein coupled receptors can be intracellularly coupled to various intracellular enzymes, ion channels and transporters. Different G-protein α-subunits preferentially stimulate particular effectors to modulate various biological functions in a cell. Phosphorylation of cytoplasmic residues of G-protein coupled receptors have been identified as an important mechanism for the regulation of G-protein coupling of the G-protein coupled receptors.

3. SUMMARY OF THE INVENTION

The present invention relates to the discovery, identification and characterization of nucleic acids that encode I5E, a novel G-protein coupled receptor protein that contains regions of homology to the neuropeptide (NPY) receptor.

The invention encompasses the following nucleotides, host cells expressing such nucleotides, and the expression products of such nucleotides: (a) nucleotides that encode mammalian I5Es, including the human I5E, and the I5E gene product; (b) nucleotides that encode portions of the I5E that correspond to its functional domains, and the polypeptide products specified by such nucleotide sequences, including but not limited to the extracellular domains (ECDs), the transmembrane domains (TMs), and the cytoplasmic domains (CDs); (c) nucleotides that encode mutants of the I5E in which all or a part of one of the domains is deleted or altered, and the polypeptide products specified by such nucleotide sequences, including but not limited to soluble receptors in which one or more of the TM domains are deleted, and nonfunctional receptors in which all or a portion of the CD is deleted; (d) nucleotides that encode fusion proteins containing the I5E or one of its domains (e.g., the extracellular domains) fused to another polypeptide.

The invention also encompasses agonists and antagonists of I5E, including small molecules, large molecules, mutant natural I5E ligand proteins that compete with native natural I5E ligand, and antibodies, as well as nucleotide sequences that can be used to inhibit I5E gene expression (e.g., antisense and ribozyme molecules, and gene or regulatory sequence replacement constructs) or to enhance I5E gene expression (e.g., expression constructs that place the I5E gene under the control of a strong promoter system), and transgenic animals that express an I5E transgene or "knock-outs" that do not express I5E.

Further, the present invention also relates to methods for the use of the I5E gene and/or I5E gene products for the identification of compounds which modulate, i.e., act as agonists or antagonists, of I5E gene expression and or I5E gene product activity. In addition, the invention relates to methods of identifying compounds suitable for treatment of diseases characterized by aberrant expression or activity levels of I5E. Such compounds can be used as therapeutic agents for use in treatment of immune disorders such as inflammation, central nervous system disorders, or metabolic disorders such as obesity, cachexia and anorexia. The invention further relates to methods of treating diseases characterized by aberrant expression or activity of I5E. The methods of treatment involve the administration of compounds that act to modulate I5E expression or I5E activity.

3.1. DEFINITIONS

As used herein, the following terms, whether used in the singular or plural, will have the meanings indicated:

I5E nucleotides or coding sequences: means nucleotide sequences encoding I5E protein, polypeptide or peptide fragments of I5E protein, or I5E fusion proteins. I5E nucleotide sequences encompass DNA, including genomic DNA (e.g. the I5E gene) or CDNA, or RNA.

I5E: means natural I5E ligand receptor protein. Polypeptides or peptide fragments of I5E protein are referred to as I5E polypeptides or I5E peptides. Fusions of I5E, or I5E polypeptides or peptide fragments to an unrelated protein are referred to herein as I5E fusion proteins.

A functional I5E refers to a protein which binds natural I5E ligand with high affinity in vivo or in vitro.

ECD: means "extracellular domain".

TM: means "transmembrane domain".

CD: means "cytoplasmic domain".

4. DESCRIPTION OF THE FIGURES

FIGS. 1A–1E. Nucleotide sequence (SEQ ID NO:1) and deduced amino acid sequence (SEQ ID NO:2) of human I5E cDNA encoding human I5E.

5. DETAILED DESCRIPTION OF THE INVENTION

I5E, described for the first time herein, is a novel G-protein coupled receptor protein that shares about 24% homology with the neuropeptide Y receptor (NPY-2 receptor) at the amino acid level. The novel I5E has been characterized as having seven hydrophobic domains which span the plasma membrane and are connected by hydrophilic extracellular and intracellular loops. In most cases, the stimulation of these receptors accelerates the turnover of phosphoinositides, with an amplitude that depends on the tissue in which the receptor is expressed.

The invention encompasses the use of I5E nucleotides, I5E proteins and peptides, as well as antibodies to I5E (which can, for example, act as I5E agonists or antagonists), antagonists that inhibit ligand binding, receptor activity or expression, or agonists that increase the binding affinity of the I5E lignad, activate receptor activity, or allow ligand to bind better or increase its expression in the diagnosis and treatment of disorders, including, but not limited to treatment of inflammatory, immune, central nervous system and metabolic disorders such as body weight disorders including obesity, cachexia and anorexia. The diagnosis of an I5E abnormality in a patient, or an abnormality in the I5E signal transduction pathway, will assist in devising a proper treatment or therapeutic regimen. In addition, I5E nucleotides and I5E proteins are useful for the identification of compounds effective in the treatment of disorders based on the aberrant expression or activity of I5E.

In particular, the invention described in the subsections below encompasses I5E, polypeptides or peptides corresponding to functional domains of the I5E (e.g., ECD, TM or CD), mutated, truncated or deleted I5Es (e.g. an I5E with one or more functional domains or portions thereof deleted, such as ΔTM and/or ΔCD), I5E fusion proteins (e.g. an I5E or a functional domain of I5E, such as one or more of the ECDs, fused to an unrelated protein or peptide such as an immunoglobulin constant region, i.e., IgFc), nucleotide sequences encoding such products, and host cell expression systems that can produce such I5E products.

The invention also encompasses antibodies and anti-idiotypic antibodies (including Fab fragments), antagonists and agonists of the I5E, as well as compounds or nucleotide constructs that inhibit expression of the I5E gene (transcription factor inhibitors, antisense and ribozyme molecules, or gene or regulatory sequence replacement constructs), or promote expression of I5E (e.g., expression constructs in which I5E coding sequences are operatively associated with expression control elements such as promoters, promoter/enhancers, etc.). The invention also relates to host cells and animals genetically engineered to express the human I5E (or mutants thereof) or to inhibit or "knock-out" expression of the animal's endogenous I5E.

The I5E proteins or peptides, I5E fusion proteins, I5E nucleotide sequences, antibodies, antagonists and agonists can be useful for the detection of mutant I5Es or inappropriately expressed I5Es for the diagnosis of disorders including immune disorders such as inflammation, central nervous system disorders, and metabolic disorders such as body weight disorders including obesity, cachexia and anorexia. The I5E proteins or peptides, I5E fusion proteins, I5E nucleotide sequences, host cell expression systems, antibodies, antagonists, agonists and genetically engineered cells and animals can be used for screening for drugs effective in the treatment of disorders. The use of engineered host cells and/or animals may offer an advantage in that such systems allow not only for the identification of compounds that bind to the ECD of the I5E, but can also identify compounds that affect the signal transduced by the activated I5E.

Finally, the I5E protein products (especially soluble derivatives such as peptides corresponding to the I5E ECD, or truncated polypeptides lacking the TM or CD domains) and fusion protein products (especially I5E-Ig fusion proteins, i.e., fusions of the I5E or a domain of the I5E, e.g., one or more ECDs, ΔTM to an IgFc), antibodies and anti-idiotypic antibodies (including Fab fragments), antagonists or agonists (including compounds that modulate signal transduction which may act on downstream targets in the I5E signal transduction pathway) can be used for therapy of such diseases. For example, the administration of an effective amount of soluble I5E ECD, ΔTM I5E or an ECD-IgFc fusion protein, or an anti-idiotypic antibody (or its Fab) that mimics the I5E ECD would "mop up" or "neutralize" endogenous ligand, and prevent or reduce binding and receptor activation. Nucleotide constructs encoding such I5E products can be used to genetically engineer host cells to express such I5E products in vivo; these genetically engineered cells function as "bioreactors" in the body delivering a continuous supply of the I5E, I5E peptide, soluble ECD or ΔTM or I5E fusion protein that will "mop up" or neutralize natural I5E ligand. Nucleotide constructs encoding functional I5Es, mutant I5Es, as well as antisense and ribozyme molecules can be used in "gene therapy" approaches for the modulation of I5E expression and/or activity in the treatment of disorders arising from the aberrant activity of the I5E.

5.1. THE I5E GENE

The cDNA sequence (SEQ. ID. No. 1) and deduced amino acid sequence (SEQ. ID. No. 2) of human I5E are shown in FIGS. 1A–1E. The I5E nucleotide sequences of the invention include: (a) the DNA sequence shown in FIGS. 1A–1E, or contained in the cDNA clone as deposited with the American Type Culture Collection (ATCC) and assigned Accession No. 98414 (b) nucleotide sequences that encode the amino acid sequence shown in FIGS. 1A–1E, or contained in the cDNA clone as deposited with the American Type Culture Collection (ATCC) and assigned Accession No. 98414 (c) any nucleotide sequence that hybridizes to the complement of the DNA sequence shown in FIGS. 1A–1E or contained in the cDNA clone as deposited with the American Type Culture Collection (ATCC) and assigned Accession No. 98414 under highly stringent conditions, e.g., hybridization to filter-bound DNA in 0.5M $NaHPO_4$, 7% sodium dodecyl sulfate (SDS), 1 mM EDTA at 65° C., and washing in 0.1× SSC/0.1% SDS at 68° C. (Ausubel F. M. et al., eds., 1989, Current Protocols in Molecular Biology, Vol. I, Green Publishing Associates, Inc., and John Wiley & sons, Inc., New York, at p. 2.10.3); (d) any nucleotide sequence that hybridizes to the complement of the DNA sequence shown in FIGS. 1A–1E or continued in the cDNA clone as deposited with the American Type Culture Collection (ATCC) and assigned Accession No. 98414 under highly stringent conditions, e.g., hybridization to filter-bound DNA in 0.5M $NaHPO_4$, 7% sodium dodecyl sulfate (SDS), 1 mM EDTA at 65° C., and washing in 0.1× SSC/0.1% SDS at 68° and encodes a functionally equivalent gene product; and (e) any nucleotide sequence that hybridizes to the complement of the DNA sequences that encode the amino acid sequence shown in FIGS. 1A–1E or contained in cDNA clone as deposited with the ATCC, under less stringent conditions, such as moderately stringent conditions, e.g., washing in 0.2× SSC/0.1% SDS at 42° C. (Ausubel et al., 1989, supra), and encodes a functionally equivalent I5E gene product. Functional equivalents of the I5E include naturally occurring I5E present in other species, and mutant I5Es whether naturally occurring or engineered. The invention also includes degenerate variants of sequences (a) through (e).

Preferred I5E nucleic acids encode polypeptides that are at least 55% identical or similar to the amino acid sequence shown in FIGS. 1A–1E or the I5E amino acid sequence encoded by the cDNA clone as deposited with the ATCC and assigned Accession No. 98414. Nucleic acids which encode polypeptides which are at least about 70%, and even more preferably at least about 80%, 85%, 90%, 95%, or 98% identical or similar with the amino acid sequence represented in FIGS. 1A–1E or the I5E amino acid sequence encoded by the cDNA clone as deposited with the ATCC and assigned Accession No. 98414 are also within the scope of the invention. In a particularly preferred embodiment, the nucleic acid of the present invention encodes a polypeptide having an overall amino acid sequence homology or identity of at least about 70%, at least about 80%, at least about 85%, at least about 90%, at least about 95%, at least about 98%, or at least 99% with the amino acid sequence shown in FIGS. 1A–1E or the I5E amino acid sequence encoded by the cDNA clone as deposited with the ATCC and assigned Accession No. 98414.

The invention also includes nucleic acid molecules, preferably DNA molecules, that hybridize to, and are therefore the complements of, the nucleotide sequences (a) through (d), in the preceding paragraph. Such hybridization conditions may be highly stringent or less highly stringent, as described above. In instances wherein the nucleic acid molecules are deoxyoligonucleotides ("oligos"), highly stringent conditions may refer, e.g., to washing in 6× SSC/0.05% sodium pyrophosphate at 37° C. (for 14-base oligos), 48° C. (for 17-base oligos), 55° C. (for 20-base oligos), and 60° C. (for 23-base oligos). These nucleic acid molecules may encode or act as I5E antisense molecules, useful, for example, in I5E gene regulation (for and/or as antisense primers in amplification reactions of I5E gene nucleic acid sequences). With respect to I5E gene regulation, such techniques can be used to regulate, for example, inflammatory disease, treatment of pain, central nervous system disorders or gastrointestinal disorders. Further, such sequences may be used as part of ribozyme and/or triple helix sequences, also useful for I5E gene regulation.

In addition to the I5E nucleotide sequences described above, full length I5E cDNA or gene sequences present in the same species and/or homologs of the I5E gene present in other species can be identified and readily isolated, without undue experimentation, by molecular biological techniques well known in the art. The identification of homologs of I5E in related species can be useful for developing animal model systems more closely related to humans for purposes of drug discovery. For example, expression libraries of cDNAs synthesized from mRNA derived from the organism of interest can be screened using labeled natural I5E ligand derived from that species, e.g., a natural I5E ligand fusion protein. Alternatively, such cDNA libraries, or genomic DNA libraries derived from the organism of interest can be screened by hybridization using the nucleotides described herein as hybridization or amplification probes. Furthermore, genes at other genetic loci within the genome that encode proteins which have extensive homology to one or more domains of the I5E gene product can also be identified via similar techniques. In the case of cDNA libraries, such screening techniques can identify clones derived from alternatively spliced transcripts in the same or different species.

Screening can be by filter hybridization, using duplicate filters. The labeled probe can contain at least 15–30 base pairs of the I5E nucleotide sequence, as shown in FIGS. 1A–1E. The hybridization washing conditions used should be of a lower stringency when the cDNA library is derived from an organism different from the type of organism from which the labeled sequence was derived. With respect to the cloning of a I5E homolog, using human I5E probes, for example, hybridization can, for example, be performed at 65° C. overnight in Church's buffer (7% SDS, 250 mM NaHPO$_4$, 2 $\mu$M EDTA, 1% BSA). Washes can be done with 2× SSC, 0.1% SDS at 65° C. and then at 0.1× SSC, 0.1% SDS at 65° C.

Low stringency conditions are well known to those of skill in the art, and will vary predictably depending on the specific organisms from which the library and the labeled sequences are derived. For guidance regarding such conditions see, for example, Sambrook et al., 1989, Molecular Cloning, A Laboratory Manual, Cold Springs Harbor Press, N.Y.; and Ausubel et al., 1989, Current Protocols in Molecular Biology, Green Publishing Associates and Wiley Interscience, N.Y.

Alternatively, the labeled I5E nucleotide probe may be used to screen a genomic library derived from the organism of interest, again, using appropriately stringent conditions. The identification and characterization of human genomic clones is helpful for designing diagnostic tests and clinical protocols for treating disorders in human patients. For example, sequences derived from regions adjacent to the intron/exon boundaries of the human gene can be used to design primers for use in amplification assays to detect mutations within the exons, introns, splice sites (e.g. splice acceptor and/or donor sites), etc., that can be used in diagnostics.

Further, an I5E gene homolog may be isolated from nucleic acid of the organism of interest by performing PCR using two degenerate oligonucleotide primer pools designed on the basis of amino acid sequences within the I5E gene product disclosed herein. The template for the reaction may be cDNA obtained by reverse transcription of mRNA prepared from cell lines or tissue known or suspected to express an I5E gene allele.

The PCR product may be subcloned and sequenced to ensure that the amplified sequences represent the sequences of an I5E gene. The PCR fragment may then be used to isolate a full length cDNA clone by a variety of methods. For example, the amplified fragment may be labeled and used to screen a cDNA library, such as a bacteriophage cDNA library. Alternatively, the labeled fragment may be used to isolate genomic clones via the screening of a genomic library.

PCR technology may also be utilized to isolate full length cDNA sequences. For example, RNA may be isolated, following standard procedures, from an appropriate cellular or tissue source (i.e., one known, or suspected, to express the I5E gene). A reverse transcription reaction may be performed on the RNA using an oligonucleotide primer specific for the most 5' end of the amplified fragment for the priming of first strand synthesis. The resulting RNA/DNA hybrid may then be "tailed" with guanines using a standard terminal transferase reaction, the hybrid may be digested with RNAase H, and second strand synthesis may then be primed with a poly-C primer. Thus, cDNA sequences upstream of the amplified fragment may easily be isolated. For a review of cloning strategies which may be used, see e.g., Sambrook et al., 1989, supra.

The I5E gene sequences may additionally be used to isolate mutant I5E gene alleles. Such mutant alleles may be isolated from individuals either known or proposed to have a genotype which contributes to the symptoms of disorders arising from the aberrant expression or activity of the I5E protein. Mutant alleles and mutant allele products may then be utilized in the therapeutic and diagnostic systems described below. Additionally, such I5E gene sequences can be used to detect I5E gene regulatory (e.g., promoter or promotor/enhancer) defects which can affect the expression of the I5E.

A cDNA of a mutant I5E gene may be isolated, for example, by using PCR, a technique which is well known to those of skill in the art. In this case, the first cDNA strand may be synthesized by hybridizing an oligo-dT oligonucleotide to mRNA isolated from tissue known or suspected to be expressed in an individual putatively carrying the mutant I5E allele, and by extending the new strand with reverse transcriptase. The second strand of the cDNA is then synthesized using an oligonucleotide that hybridizes specifically to the 5' end of the normal gene. Using these two primers, the product is then amplified via PCR, cloned into a suitable vector, and subjected to DNA sequence analysis through methods well known to those of skill in the art. By comparing the DNA sequence of the mutant I5E allele to that of the normal I5E allele, the mutation(s) responsible for the loss or alteration of function of the mutant I5E gene product can be ascertained.

Alternatively, a genomic library can be constructed using DNA obtained from an individual suspected of or known to carry the mutant I5E allele, or a cDNA library can be constructed using RNA from a tissue known, or suspected, to express the mutant I5E allele. The normal I5E gene or any suitable fragment thereof may then be labeled and used as a probe to identify the corresponding mutant I5E allele in such libraries. Clones containing the mutant I5E gene sequences may then be purified and subjected to sequence analysis according to methods well known to those of skill in the art.

Additionally, an expression library can be constructed utilizing cDNA synthesized from, for example, RNA isolated from a tissue known, or suspected, to express a mutant I5E allele in an individual suspected of or known to carry such a mutant allele. In this manner, gene products made by the putatively mutant tissue may be expressed and screened using standard antibody screening techniques in conjunction with antibodies raised against the normal I5E gene product, as described, below, in Section 5.3. (For screening techniques, see, for example, Harlow, E. and Lane, eds., 1988, "Antibodies: A Laboratory Manual", Cold Spring Harbor Press, Cold Spring Harbor.) Additionally, screening can be accomplished by screening with labeled natural I5E ligand fusion proteins, such as, for example, AP-natural I5E ligand or natural I5E ligand-AP fusion proteins. In cases where an I5E mutation results in an expressed gene product with altered function (e.g., as a result of a missense or a frameshift mutation), a polyclonal set of antibodies to I5E are likely to cross-react with the mutant I5E gene product. Library clones detected via their reaction with such labeled antibodies can be purified and subjected to sequence analysis according to methods well known to those of skill in the art.

The invention also encompasses nucleotide sequences that encode mutant I5Es, peptide fragments of the I5E, truncated I5Es, and I5E fusion proteins. These include, but are not limited to nucleotide sequences encoding mutant I5Es described in section 5.2 infra; polypeptides or peptides corresponding to one or more of the ECDs, or TM and/or CD domains of the I5E or portions of these domains; truncated I5Es in which one or two of the domains is deleted, e.g., a soluble I5E lacking a TM domain, or both a TM and CD regions, or a truncated, nonfunctional I5E lacking all, or a portion of a CD region. Nucleotides encoding fusion proteins may include by are not limited to full length I5E, truncated I5E or peptide fragments of I5E fused to an unrelated protein or peptide, such as for example, a transmembrane sequence, which anchors the I5E ECD to the cell membrane; an Ig Fc domain which increases the stability and half life of the resulting fusion protein (e.g., I5E-Ig) in the bloodstream; or an enzyme, fluorescent protein, luminescent protein which can be used as a marker.

The invention also encompasses (a) DNA vectors that contain any of the foregoing I5E coding sequences and/or their complements (i.e., antisense); (b) DNA expression vectors that contain any of the foregoing I5E coding sequences operatively associated with a regulatory element that directs the expression of the coding sequences; and (c) genetically engineered host cells that contain any of the foregoing I5E coding sequences operatively associated with a regulatory element that directs the expression of the coding sequences in the host cell. As used herein, regulatory elements include but are not limited to inducible and non-inducible promoters, enhancers, operators and other elements known to those skilled in the art that drive and regulate expression. Such regulatory elements include but are not limited to the cytomegalovirus hCMV immediate early gene, the early or late promoters of SV40 adenovirus, the lac system, the trp system, the TAC system, the TRC system, the major operator and promoter regions of phage A, the control regions of fd coat protein, the promoter for 3-phosphoglycerate kinase, the promoters of acid phosphatase, and the promoters of the yeast α-mating factors.

5.2. I5E PROTEINS AND POLYPEPTIDES

I5E protein, polypeptides and peptide fragments, mutated, truncated or deleted forms of the I5E and/or I5E fusion proteins can be prepared for a variety of uses, including but not limited to the generation of antibodies, as reagents in diagnostic assays, the identification of other cellular gene products involved in the regulation of the I5E, as reagents in assays for screening for compounds that can be used in the treatment of I5E related disorders, and as pharmaceutical reagents useful in the treatment of disorders related to the I5E.

FIGS. 1A–1E shows the amino acid sequence of the human I5E protein. The I5E amino acid sequences of the invention include the amino acid sequence shown in FIGS. 1A–1E (SEQ. ID. No:2) or the amino acid sequence encoded by DNA as deposited with the ATCC and assigned Accession No. 98414. Polypeptides which are at least about 70%, and even more preferably at least about 80%, 85%, 90%, 95% or 98% identical or similar with the amino acid sequence represented by FIGS. 1A–1E or the amino acid sequence encoded by the cDNA clone as deposited with the ATCC and assigned Accession No. 98414 are encompassed by the invention. Further, I5Es of other species are encompassed by the invention. In fact, any I5E protein encoded by the I5E nucleotide sequences described in Section 5.1, above, are within the scope of the invention.

The invention also encompasses proteins that are functionally equivalent to the I5E encoded by the nucleotide sequences described in Section 5.1, as judged by any of a number of criteria, including but not limited to the ability to bind natural I5E ligand, the binding affinity for natural I5E ligand, the resulting biological effect of natural I5E ligand binding, e.g., signal transduction, a change in cellular metabolism (e.g., ion flux, tyrosine phosphorylation) or change in phenotype when the I5E equivalent is present in an appropriate cell type. Such functionally equivalent I5E proteins include but are not limited to additions or substitutions of amino acid residues within the amino acid sequence encoded by the I5E nucleotide sequences described, above, in Section 5.1, but which result in a silent change, thus producing a functionally equivalent gene product. Amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

While random mutations can be made to I5E DNA (using random mutagenesis techniques well known to those skilled in the art) and the resulting mutant I5Es tested for activity, site-directed mutations of the I5E coding sequence can be engineered (using site-directed mutagenesis techniques well known to those skilled in the art) to generate mutant I5Es with increased function, e.g., higher binding affinity for natural I5E ligand, and/or greater signalling capacity; or decreased function, e.g., lower binding affinity for natural I5E ligand, and/or decreased signal transduction capacity.

For example, regions of identity may be determined by alignment of human I5E (FIGS. 1A–1E) with I5E homologs from other species. Mutant I5Es can be engineered so that regions of identity are maintained, whereas the variable residues are altered, e.g., by deletion or insertion of an amino acid residue(s) or by substitution of one or more different amino acid residues. Conservative alterations at the variable positions can be engineered in order to produce a mutant I5E that retains function; e.g., natural I5E ligand binding affinity or signal transduction capability or both. Nonconservative changes can be engineered at these variable positions to alter function, e.g., natural I5E ligand binding affinity or signal transduction capability, or both. Alternatively, where alteration of function is desired, deletion or non-conservative alterations of the conserved regions can be engineered. For example, deletion or non-conservative alterations (substitutions or insertions) of the CD, e.g., amino acid residues of human I5E, or amino acid residues, or portions of the CD, of the human I5E (FIGS. 1A–1E). Non-conservative alterations to the ECD shown can be engineered to produce mutant I5Es with altered binding affinity for natural I5E ligand. The same mutation strategy can also be used to design mutant I5Es based on the alignment of human I5E and I5E homologs from other species.

Other mutations to the I5E coding sequence can be made to generate I5Es that are better suites for expression, scale up, etc. in the host cells chosen. For example, cysteine residues can be deleted or substituted with another amino acid in order to eliminate disulfide bridges; N-linked glycosylation sites can be altered or eliminated to achieve, for example, expression of a homogeneous product that is more easily recovered and purified from yeast hosts which are known to hyperglycosylate N-linked sites. To this end, a variety of amino acid substitutions at one or both of the first or third amino acid positions of any one or more of the glycosylation recognition sequences which occur in the ECD (N-X-S or N-X-T), and/or an amino acid deletion at the second position of any one or more such recognition sequences in the ECD will prevent glycosylation of the I5E at the modified tripeptide sequence. (See, e.g., Miyajima et al., 1986, EMBO J. 5(6):1193–1197).

The amino acid sequence of the I5E has a serpentine structure containing hydrophilic domains located between the TM domains, arranged alternately outside and within the cell to form the ECD and CD of the receptor.

Peptides corresponding to one or more domains of the I5E (e.g., ECD, TM or CD), truncated or deleted I5Es (e.g., I5E in which the TM and/or CD is deleted) as well as fusion proteins in which the full length I5E, an I5E peptide or truncated I5E is fused to an unrelated protein are also within the scope of the invention and can be designed on the basis of the I5E nucleotide and I5E amino acid sequences disclosed in this Section and in Section 5.1, above. Such fusion proteins include but are not limited to IgFc fusions which stabilize the I5E protein or peptide and prolong half-life in vivo; or fusions to any amino acid sequence that allows the fusion protein to be anchored to the cell membrane, allowing the ECD to be exhibited on the cell surface; or fusions to an enzyme, fluorescent protein, or luminescent protein which provide a marker function.

Such I5E polypeptides, peptides and fusion proteins can be produced by recombinant DNA technology using techniques well known in the art for expressing nucleic acid containing I5E gene sequences and/or coding sequences. For example, nucleotide sequences encoding one or more of the domains of the I5E ECD of the serpentine I5E can be synthesized or cloned and ligated together to create a soluble ECD of the I5E. The DNA sequence endcoding one or more of the ECDs can be ligated together directly or via a linker oligonucleotide that encodes a peptide spacer. Such linkers may encode flexible, glycine-rich amino acid sequences thereby alluring the domains that are strung together to assume a conformation that can bind the natural I5E ligand. Alternatively, nucleotide sequences encoding individual domains within the ECD can be used to express I5E peptides. A variety of methods can be used to construct expression vectors containing the I5E nucleotide sequences as described in Section 5.1 and appropriate transcriptional and translational control signals. These methods include, for example, in vitro recombinant DNA techniques, synthetic techniques, and in vivo genetic recombination. See, for example, the techniques described in Sambrook et al., 1989, supra, and Ausubel et al., 1989, supra. Alternatively, RNA capable of encoding I5E nucleotide sequences may be chemically synthesized using, for example, synthesizers. See, for example, the techniques described in "Oligonucleotide Synthesis", 1984, Gait, M. J. ed., IRL Press, Oxford, which is incorporated by reference herein in its entirety.

A variety of host-expression vector systems may be utilized to express the I5E nucleotide sequences of the invention. Where the I5E peptide or polypeptide is a soluble derivative (e.g., I5E peptides corresponding to the ECD; truncated or deleted I5E in which the TM and/or CD are deleted) the peptide or polypeptide can be recovered from the culture, i.e., from the host cell in cases where the I5E peptide or polypeptide is not secreted, and from the culture media in cases where the I5E peptide or polypeptide is secreted by the cells. However, the expression systems also encompass engineered host cells that express the I5E or functional equivalents in situ, i.e., anchored in the cell membrane. Purification or enrichment of the I5E from such expression systems can be accomplished using appropriate detergents and lipid micelles and methods well known to those skilled in the art. However, such engineered host cells themselves may be used in situations where it is important not only to retain the structural and functional characteristics of the I5E, but to assess biological activity, e.g., in drug screening assays.

The expression systems that may be used for purposes of the invention include but are not limited to microorganisms such as bacteria (e.g., *E. coli, B. subtilis*) transformed with recombinant bacteriophage DNA, plasmid DNA or cosmid DNA expression vectors containing I5E nucleotide sequences; yeast (e.g., Saccharomyces, Pichia) transformed with recombinant yeast expression vectors containing the I5E nucleotide sequences; insect cell systems infected with recombinant virus expression vectors (e.g., baculovirus) containing the I5E sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing I5E nucleotide sequences; or mammalian cell systems (e.g., COS, CHO, BHK, 293, 3T3) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors may be advantageously selected depending upon the use intended for the I5E gene product being expressed. For example, when a large quantity of such a protein is to be produced, for the generation of pharmaceutical compositions of I5E protein or for raising antibodies to the I5E protein, for example, vectors which direct the expression of high levels of fusion protein products that are readily purified may be desirable. Such vectors include, but are not limited to, the *E. coli* expression vector pUR278 (Ruther et al., 1983, EMBO J. 2:1791), in which the I5E coding sequence may be ligated individually into the vector in frame with the lacZ coding region so that a fusion protein is produced; pIN vectors (Inouye & Inouye, 1985, Nucleic Acids Res. 13:3101–3109; Van Heeke & Schuster, 1989, J. Biol. Chem. 264:5503–5509); and the like. pGEX vectors may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The PGEX vectors are designed to include thrombin or factor Xa protease cleavage sites so that the cloned target gene product can be released from the GST moiety.

In an insect system, *Autographa californica* nuclear polyhidrosis virus (AcNPV) is used as a vector to express foreign genes. The virus grows in *Spodoptera frugiperda* cells. The I5E gene coding sequence may be cloned individually into non-essential regions (for example the polyhedrin gene) of the virus and placed under control of an AcNPV promoter (for example the polyhedrin promoter). Successful insertion of I5E gene coding sequence will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed. (E.g, see Smith et al., 1983, J. Virol. 46: 584; Smith, U.S. Pat. No. 4,215,051).

In mammalian host cells, a number of viral-based expression systems may be utilized. In cases where an adenovirus is used as an expression vector, the I5E nucleotide sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the I5E gene product in infected hosts. (E.g., See Logan & Shenk, 1984, Proc. Natl. Acad. Sci. USA 81:3655–3659). Specific initiation signals may also be required for efficient translation of inserted I5E nucleotide sequences. These signals include the ATG initiation codon and adjacent sequences. In cases where an entire I5E gene or cDNA, including its own initiation codon and adjacent sequences, is inserted into the appropriate expression vector, no additional translational control signals may be needed. However, in cases where only a portion of the I5E coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (See Bittner et al., 1987, Methods in Enzymol. 153:516–544).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERO, BHK, HeLa, COS, MDCK, 293, 3T3 and WI38.

For long-term, high-yield production of recombinant proteins, stable expression is preferred. For example, cell lines which stably express the I5E sequences described above may be engineered. Rather than using expression vectors which contain viral origins of replication, host cells can be transformed with DNA controlled by appropriate expression control elements (e.g., promoter, enhancer sequences, transcription terminators, polyadenylation sites, etc.), and a selectable marker. Following the introduction of the foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the I5E gene product. Such engineered cell lines may be particularly useful in screening and evaluation of compounds that affect the endogenous activity of the I5E gene product.

A number of selection systems may be used, including but not limited to the herpes simplex virus thymidine kinase (Wigler, et al., 1977, Cell 11:223), hypoxanthine-guanine phosphoribosyltransferase (Szybalska & Szybalski, 1962, Proc. Natl. Acad. Sci. USA 48:2026), and adenine phosphoribosyltransferase (Lowy, et al., 1980, Cell 22:817) genes can be employed in tk$^-$, hgprt$^-$ or aprt$^-$ cells, respectively. Also, antimetabolite resistance can be used as the basis of selection for the following genes: dhfr, which confers resistance to methotrexate (Wigler, et al., 1980, Natl. Acad. Sci. USA 77:3567; O'Hare, et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Colberre-Garapin, et al., 1981, J. Mol. Biol. 150:1); and hygro, which confers resistance to hygromycin (Santerre, et al., 1984, Gene 30:147).

Alternatively, any fusion protein may be readily purified by utilizing an antibody specific for the fusion protein being expressed. For example, a system described by Janknecht et al. allows for the ready purification of non-denatured fusion proteins expressed in human cell lines (Janknecht, et al., 1991, Proc. Natl. Acad. Sci. USA 88: 8972–8976). In this system, the gene of interest is subcloned into a vaccinia recombination plasmid such that the gene's open reading frame is translationally fused to an amino-terminal tag consisting of six histidine residues. Extracts from cells infected with recombinant vaccinia virus are loaded onto $Ni^{2+}$. nitriloacetic acid-agarose columns and histidine-tagged proteins are selectively eluted with imidazole-containing buffers.

The I5E gene products can also be expressed in transgenic animals. Animals of any species, including, but not limited to, mice, rats, rabbits, guinea pigs, pigs, micro-pigs, goats, and non-human primates, e.g., baboons, monkeys, and chimpanzees may be used to generate I5E transgenic animals.

Any technique known in the art may be used to introduce the I5E transgene into animals to produce the founder lines of transgenic animals. Such techniques include, but are not limited to pronuclear microinjection (Hoppe, P.C. and Wagner, T. E., 1989, U.S. Pat. No. 4,873,191); retrovirus mediated gene transfer into germ lines (Van der Putten et al., 1985, Proc. Natl. Acad. Sci., USA 82:6148–6152); gene targeting in embryonic stem cells (Thompson et al., 1989, Cell 56:313–321); electroporation of embryos (Lo, 1983, Mol Cell. Biol. 3:1803–1814); and sperm-mediated gene transfer (Lavitrano et al., 1989, Cell 57:717–723); etc. For a review of such techniques, see Gordon, 1989, Transgenic Animals, Intl. Rev. Cytol. 115:171–229, which is incorporated by reference herein in its entirety.

The present invention provides for transgenic animals that carry the I5E transgene in all their cells, as well as animals which carry the transgene in some, but not all their cells, i.e., mosaic animals. The transgene may be integrated as a single transgene or in concatamers, e.g., head-to-head tandems or head-to-tail tandems. The transgene may also be selectively introduced into and activated in a particular cell type by following, for example, the teaching of Lasko et al. (Lasko, M. et al., 1992, Proc. Natl. Acad. Sci. USA 89: 6232–6236). The regulatory sequences required for such a cell-type specific activation will depend upon the particular cell type of interest, and will be apparent to those of skill in the art. When it is desired that the I5E gene transgene be integrated into the chromosomal site of the endogenous I5E gene, gene targeting is preferred. Briefly, when such a technique is to be utilized, vectors containing some nucleotide sequences homologous to the endogenous I5E gene are designed for the purpose of integrating, via homologous recombination with chromosomal sequences, into and disrupting the function of the nucleotide sequence of the endogenous I5E gene. The transgene may also be selectively introduced into a particular cell type, thus inactivating the endogenous I5E gene in only that cell type, by following, for example, the teaching of Gu et al. (Gu, et al., 1994, Science 265: 103–106). The regulatory sequences required for such a cell-type specific inactivation will depend upon the particular cell type of interest, and will be apparent to those of skill in the art.

Once transgenic animals have been generated, the expression of the recombinant I5E gene may be assayed utilizing standard techniques. Initial screening may be accomplished by Southern blot analysis or PCR techniques to analyze animal tissues to assay whether integration of the transgene has taken place. The level of mRNA expression of the transgene in the tissues of the transgenic animals may also be assessed using techniques which include but are not limited to Northern blot analysis of tissue samples obtained from the animal, in situ hybridization analysis, and RT-PCR. Samples of I5E gene-expressing tissue, may also be evaluated immunocytochemically using antibodies specific for the I5E transgene product.

5.3. ANTIBODIES TO I5E PROTEINS

Antibodies that specifically recognize one or more epitopes of I5E, or epitopes of conserved variants of I5E, or peptide fragments of the I5E are also encompassed by the invention. Such antibodies include but are not limited to polyclonal antibodies, monoclonal antibodies (mAbs), humanized or chimeric antibodies, single chain antibodies, Fab fragments, F(ab')$_2$ fragments, fragments produced by a Fab expression library, anti-idiotypic (anti-Id) antibodies, and epitope-binding fragments of any of the above.

The antibodies of the invention may be used, for example, in the detection of the I5E in a biological sample and may, therefore, be utilized as part of a diagnostic or prognostic technique whereby patients may be tested for abnormal amounts of I5E. Such antibodies may also be utilized in conjunction with, for example, compound screening schemes, as described, below, in Section 5.5, for the evaluation of the effect of test compounds on expression and/or activity of the I5E gene product. Additionally, such antibodies can be used in conjunction with the gene therapy techniques described, below, in Section 5.6, to, for example, evaluate the normal and/or engineered I5E-expressing cells prior to their introduction into the patient. Such antibodies may additionally be used as a method for the inhibition of abnormal I5E activity.

For the production of antibodies, various host animals may be immunized by injection with the I5E, an I5E peptide (e.g., one corresponding the a functional domain of the receptor, such as ECD, TM or CD), truncated I5E polypeptides (I5E in which one or more domains, e.g., the TM or CD, has been deleted), functional equivalents of the I5E or mutants of the I5E. Such host animals may include but are not limited to rabbits, mice, and rats, to name but a few. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*. Polyclonal antibodies are heterogeneous populations of antibody molecules derived from the sera of the immunized animals.

Monoclonal antibodies, which are homogeneous populations of antibodies to a particular antigen, may be obtained by any technique which provides for the production of antibody molecules by continuous cell lines in culture. These include, but are not limited to, the hybridoma technique of Kohler and Milstein, (1975, Nature 256:495–497; and U.S. Pat. No. 4,376,110), the human B-cell hybridoma technique (Kosbor et al., 1983, Immunology Today 4:72; Cole et al., 1983, Proc. Natl. Acad. Sci. USA 80:2026–2030), and the EBV-hybridoma technique (Cole et al., 1985, Monoclonal Antibodies And Cancer Therapy, Alan R. Liss, Inc., pp. 77–96). Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

In addition, techniques developed for the production of "chimeric antibodies" (Morrison et al., 1984, Proc. Natl. Acad. Sci., 81:6851–6855; Neuberger et al., 1984, Nature, 312:604–608; Takeda et al., 1985, Nature, 314:452–454) by splicing the genes from a mouse antibody molecule of appropriate antigen specificity together with genes from a human antibody molecule of appropriate biological. activity can be used. A chimeric antibody is a molecule in which different portions are derived from different animal species, such as those having a variable region derived from a murine mAb and a human immunoglobulin constant region.

In addition, techniques have been developed for the production of humanized antibodies. (See, e.g., Queen, U.S. Pat. No. 5,585,089, which is incorporated herein by reference in its entirety.) An immunoglobulin light or heavy chain variable region consists of a "framework" region interrupted by three hypervariable regions, referred to as complementarily determining regions (CDRs). The extent of the framework region and CDRs have been precisely defined (see, "sequences of Proteins of Immunological Interest", Kabat, E. et al., U.S. Department of Health and Human Services (1983). Briefly, humanized antibodies are antibody molecules from non-human species having one or more CDRs from the non-human species and a framework region from a human immunoglobulin molecule.

Alternatively, techniques described for the production of single chain antibodies (U.S. Pat. No. 4,946,778; Bird, 1988, Science 242:423–426; Huston et al., 1988, Proc. Natl. Acad. Sci. USA 85:5879–5883; and Ward et al., 1989, Nature 334:544–546) can be adapted to produce single chain antibodies against I5E gene products. Single chain antibodies are formed by linking the heavy and light chain fragments of the Fv region via an amino acid bridge, resulting in a single chain polypeptide.

Antibody fragments which recognize specific epitopes may be generated by known techniques. For example, such fragments include but are not limited to: the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed (Huse et al., 1989, Science, 246:1275–1281) to allow rapid and easy identification of monoclonal Fab fragments with the desired specificity.

Antibodies to the I5E can, in turn, be utilized to generate anti-idiotype antibodies that "mimic" the I5E, using techniques well known to those skilled in the art. (See, e.g., Greenspan & Bona, 1993, FASEB J 7(5):437–444; and Nissinoff, 1991, J. Immunol. 147(8):2429–2438). For example antibodies which bind to the I5E ECD and competitively inhibit the binding of natural I5E ligand to the I5E can be used to generate anti-idiotypes that "mimic" the ECD and, therefore, bind and neutralize natural I5E ligand. Such neutralizing anti-idiotypes or Fab fragments of such anti-idiotypes can be used in therapeutic regimens to neutralize the physiological activity of the natural gpc-R ligand.

5.4. SCREENING ASSAYS FOR COMPOUNDS THAT MODULATE I5E EXPRESSION OR ACTIVITY

The following assays are designed to identify compounds that are capable of modulating the expression or biological activity of I5E. Such compounds can be used to treat diseases arising from aberrant expression or activity of the I5E. Such diseases include immune disorders such as inflammation, central nervous system disorders or metabolic disorders such as those involved in body weight disorders, including but not limited to obesity, cachexia and anorexia.

The following assays are designed to identify compounds that interact with (e.g., bind to) I5E (including, but not limited to the ECD or CD of I5E), compounds that interact with (e.g., bind to) intracellular proteins that interact with I5E (including, but not limited to, the TM and CD of I5E), compounds that interfere with the interaction of I5E with transmembrane or intracellular proteins involved in I5E-mediated signal transduction, and to compounds which modulate the activity of I5E gene (i.e., modulate the level of I5E gene expression) or modulate the level of I5E. Such assays may be used to identify compounds that function as antagonist or agonists of I5E activity. Assays may additionally be utilized which identify compounds which bind to I5E gene regulatory sequences (e.g., promoter sequences) and which may modulate I5E gene expression. See e.g., Platt, K. A., 1994, J. Biol. Chem. 269:28558–28562, which is incorporated herein by reference in its entirety.

The compounds which may be screened in accordance with the invention include, but are not limited to peptides, antibodies and fragments thereof, and other organic compounds (e.g., peptidomimetics) that interact with (i.e., bind to) the ECD of the I5E and either mimic the activity triggered by the natural ligand (i.e., agonists) or inhibit the activity triggered by the natural ligand (i.e., antagonists); as well as peptides, antibodies or fragments thereof, and other organic compounds that mimic the ECD of the I5E (or a portion thereof) and bind to and "neutralize" natural ligand. Such compounds may include, but are not limited to, peptides such as, for example, soluble peptides, including but not limited to members of random peptide libraries; (see, e.g., Lam, K. S. et al., 1991, Nature 354:82–84; Houghten, R. et al., 1991, Nature 354:84–86), and combinatorial chemistry-derived molecular library made of D- and/or L-configuration amino acids, phosphopeptides (including, but not limited to, members of random or partially degenerate, directed phosphopeptide libraries; see, e.g., Songyang, Z. et al., 1993, Cell 72:767–778); molecules from natural product libraries, antibodies (including, but not limited to, polyclonal, monoclonal, humanized, anti-idiotypic, chimeric or single chain antibodies, and FAb, F(ab')$_2$ and FAb expression library fragments, and epitope-binding fragments thereof), and small organic or inorganic molecules.

Other compounds which can be screened in accordance with the invention include but are not limited to small organic molecules that are able to cross the blood-brain barrier, gain entry into an appropriate cell and affect the expression of the I5E gene or some other gene involved in the I5E signal transduction pathway (e.g., by interacting with the regulatory region or transcription factors involved in gene expression); or such compounds that affect the activity of the I5E or the activity of some other intracellular factor involved in the I5E signal transduction pathway.

5.4.1 ANIMAL-AND CELL-BASED MODEL SYSTEMS

Described herein are cell- and animal-based systems which act as models for disorders arising from aberrant expression or activity of I5E. Cell- and animal-based model systems can also be used to further characterize the activity of the I5E gene. Such assays can be utilized as part of screening strategies designed to identify compounds which are capable of ameliorating I5E based disorders such as immune disorders, central nervous system disorders or metabolic disorders such as those involved in body weight disorders, including but not limited to obesity, cachexia and anorexia. Thus, the animal- and cell-based models can be used to identify drugs, pharmaceuticals, therapies and interventions which can be effective in treating disorders aberrant expression or activity of the I5E cytokine. In addition, as described in detail, below, in Section 5.7.1, such animal models can be used to determine the $LD_{50}$ and the $ED_{50}$ in animal subjects, and such data can be used to determine the in vivo efficacy of potential I5E disorder treatments.

Animal-based model systems of I5E based disorders such as, but not limited to, TH cell subpopulation-related disorders, based on aberrant I5E expression or activity, can include both non-recombinant animals as well as recombinantly engineered transgenic animals.

Animal models for I5E disorders can include, for example, genetic models. Animal models exhibiting I5E based disorder-like symptoms can be engineered by utilizing, for example, I5E sequences such as those described, above, in Section 5.2, in conjunction with techniques for producing transgenic animals that are well known to those of skill in the art. For example, I5E sequences can be introduced into, and overexpressed and/or misexpressed in, the genome of the animal of interest, or, if endogenous I5E sequences are present, they can either be overexpressed, misexpressed, or, alternatively, can be disrupted in order to underexpress or inactivate I5E gene expression.

In order to overexpress or misexpress a I5E gene sequence, the coding portion of the I5E gene sequence can be ligated to a regulatory sequence which is capable of driving high level gene expression or expression in a cell type in which the gene is not normally expressed in the animal and/or cell type of interest. Such regulatory regions will be well known to those of skill in the art, and can be utilized in the absence of undue experimentation.

For underexpression of an endogenous I5E gene sequence, such a sequence can be isolated and engineered such that when reintroduced into the genome of the animal of interest, the endogenous I5E gene alleles will be inactivated. Preferably, the engineered I5E gene sequence is introduced via gene targeting such that the endogenous I5E sequence is disrupted upon integration of the engineered I5E gene sequence into the animal's genome. Gene targeting is discussed, below, in this Section.

Animals of any species, including, but not limited to, mice, rats, rabbits, guinea pigs, pigs, micro-pigs, goats, and non-human primates, e.g., baboons, squirrels, monkeys, and chimpanzees can be used to generate animal models of I5E-related disorders.

Any technique known in the art can be used to introduce a I5E transgene into animals to produce the founder lines of transgenic animals. Such techniques include, but are not limited to pronuclear microinjection (Hoppe, P. C. and Wagner, T. E., 1989, U.S. Pat. No. 4,873,191); retrovirus mediated gene transfer into germ lines (Van der Putten et al., 1985, Proc. Natl. Acad. Sci., USA 82:6148–6152); gene targeting in embryonic stem cells (Thompson et al., 1989, Cell 56:313–321); electroporation of embryos (Lo, 1983, Mol Cell. Biol. 3:1803–1814); and sperm-mediated gene transfer (Lavitrano et al., 1989, Cell 57:717–723); etc. For a review of such techniques, see Gordon, 1989, Transgenic Animals, Intl. Rev. Cytol. 115:171–229, which is incorporated by reference herein in its entirety.

The present invention provides for transgenic animals that carry the I5E transgene in all their cells, as well as animals which carry the transgene in some, but not all their cells, i.e., mosaic animals. (See, for example, techniques described by Jakobovits, 1994, Curr. Biol. 4:761–763.) The transgene can be integrated as a single transgene or in concatamers, e.g., head-to-head tandems or head-to-tail tandems. The transgene can also be selectively introduced into and activated in a particular cell type by following, for example, the teaching of Lasko et al. (Lasko, M. et al., 1992, Proc. Natl. Acad. Sci. USA 89:6232–6236). The regulatory sequences required for such a cell-type specific activation will depend upon the particular cell type of interest, and will be apparent to those of skill in the art.

When it is desired that the I5E transgene be integrated into the chromosomal site of the endogenous I5E gene, gene targeting is preferred. Briefly, when such a technique is to be utilized, vectors containing some nucleotide sequences homologous to the endogenous I5E gene of interest are designed for the purpose of integrating, via homologous recombination with chromosomal sequences, into and disrupting the function of, the nucleotide sequence of the endogenous I5E gene. The transgene can also be selectively introduced into a particular cell type, thus inactivating the endogenous gene of interest in only that cell type, by following, for example, the teaching of Gu et al. (Gu, H. et al., 1994, Science 265:103–106). The regulatory sequences required for such a cell-type specific inactivation will depend upon the particular cell type of interest, and will be apparent to those of skill in the art.

Once transgenic animals have been generated, the expression of the recombinant I5E gene and protein can be assayed utilizing standard techniques. Initial screening can be accomplished by Southern blot analysis or PCR techniques to analyze animal tissues to assay whether integration of the transgene has taken place. The level of mRNA expression of the I5E transgene in the tissues of the transgenic animals can also be assessed using techniques which include but are not limited to Northern blot analysis of tissue samples obtained from the animal, in situ hybridization analysis, and RT-PCR. Samples of target gene-expressing tissue, can also be evaluated immunocytochemically using antibodies specific for the target gene transgene gene product of interest.

The I5E transgenic animals that express I5E gene mRNA or I5E transgene peptide (detected immunocytochemically, using antibodies directed against target gene product epitopes) at easily detectable levels can then be further evaluated to identify those animals which display characteristic I5E based disorder symtoms.

Once I5E transgenic founder animals are produced (i.e., those animals which express I5E proteins in cells or tissues of interest, and which, preferably, exhibit symptoms of I5E based disorders), they can be bred, inbred, outbred, or crossbred to produce colonies of the particular animal. Examples of such breeding strategies include but are not limited to: outbreeding of founder animals with more than one integration site in order to establish separate lines; inbreeding of separate lines in order to produce compound I5E transgenics that express the I5E transgene of interest at higher levels because of the effects of additive expression of each I5E transgene; crossing of heterozygous transgenic animals to produce animals homozygous for a given integration site in order to both augment expression and eliminate the possible need for screening of animals by DNA analysis; crossing of separate homozygous lines to produce compound heterozygous or homozygous lines; breeding animals to different inbred genetic backgrounds so as to examine effects of modifying alleles on expression of the I5E transgene and the development of I5E-like symptoms. One such approach is to cross the I5E transgenic founder animals with a wild type strain to produce an F1 generation that exhibits I5E related disorder-like symptoms, such as those described above. The F1 generation can then be inbred in order to develop a homozygous line, if it is found that homozygous target gene transgenic animals are viable.

Cells that contain and express I5E sequences which encode I5E protein, and, further, exhibit cellular phenotypes associated with a I5E based disorder can be utilized to identify compounds that exhibit an ability to ameliorate I5E-related disorder symptoms.

Further, the fingerprint pattern of gene expression of cells of interest can be analyzed and compared to the normal, non-I5E-related disorder fingerprint pattern. Those compounds which cause cells exhibiting I5E-related disorder-like cellular phenotypes to produce a fingerprint pattern more closely resembling a normal fingerprint pattern for the cell of interest can be considered candidates for further testing regarding an ability to ameliorate I5E-related disorder symptoms.

In accordance with the invention, a cell-based assay system can be used to screen for compounds that modulate the activity of the I5E. To this end, cells that endogenously express I5E can be used to screen for compounds. Alternatively, cell lines, such as 293 cells, COS cells, CHO cells, fibroblasts, and the like, genetically engineered to express the I5E can be used for screening purposes. Preferably, host cells genetically engineered to express a functional receptor that responds to activation by the natural I5E ligand can be used as an endpoint in the assay; e.g., as measured by a chemical, physiological, biological, or phenotypic change, induction of a host cell gene or a reporter gene, change in cAMP levels, adenylyl cyclase activity, host cell G protein activity, extracellular acidification rate, host cell kinase activity, proliferation, differentiation, etc.

To be useful in screening assays, the host cells expressing functional I5E should give a significant response to I5E ligand, preferably greater than 5-fold induction over background.

In utilizing such cell systems, the cells expressing the I5E are exposed to a test compound or to vehicle controls (e.g., placebos). After exposure, the cells can be assayed to measure the expression and/or activity of components of the signal transduction pathway of the I5E, or the activity of the signal transduction pathway itself can be assayed. For example, after exposure, cell lysates can be assayed for induction of phospholipase C or accumulation of inositol phosphate (IP) in the cell. The ability of a test compound to increase levels of phospholipase C or inositol phosphate, above those levels seen with cells treated with a vehicle control, indicates that the test compound induces signal transduction mediated by the I5E expressed by the host cell.

To determine intracellular inositol phosphate concentrations, an assay that utilizes [$^3$H] inositol and anion exchange columns containing AG 1-X8 resin may be used as described in Tian et al. (1996, J.Neurochemistry 67:1191–1199). The assay may be performed in 96-well plates to enable high-throughput screening and 96 well-based scintillation counting instruments such as those manufactured by Wallac or Packard may be used for readout.

Other screening techniques include the use of cells which express the G-protein coupled receptor (for example, transfected CHO cells) in a system which measures extracellular pH changes caused by receptor activation, for example, as described in Science, volume 246, pages 181–296 (October 1989). In addition, a cytosensor microphysiometer can be used to detect and monitor the response of cells to chemical substances as described in McConnell et al. (1992, Science 257: 1906–1912). For example, potential agonists or antagonists may be contacted with a cell which expresses the G-protein coupled receptor and a second messenger response, e.g., signal transduction or pH changes, may be measured to determine whether the potential agonist or antagonist is effective.

Yet another screening procedure involves the use of the melanophores which are transfected to express the G-protein coupled receptor of the present invention. Such a screening technique is described in PCT WO 92/01810 published Feb. 6, 1992.

Thus, for example, such an assay may be employed for screening for a receptor antagonist by contacting the melanophore cells which encode the 5-protein coupled receptor with both the receptor ligand and a compound to be screened. Inhibition of the signal generated by the ligand indicates that a compound is a potential antagonist for the receptor, i.e., inhibits activation of the receptor. The screen may also be employed for determining an agonist by contacting such cells with compounds to be screened and determining whether such compound generates a signal, i.e., activates the receptor.

Another such screening technique involves introducing RNA encoding I5E into Xenopus oocytes to transiently express the receptor. The receptor expressing oocytes may then be contacted, in the case of antagonist screening, with the receptor ligand and a compound to be screened, followed by detection of inhibition of a calcium signal.

Another method involves screening for antagonists by determining inhibition of binding a labeled ligand to cells which have the receptor on the surface thereof. Such a method involves transfecting a eukaryotic cell with DNA encoding the G-protein coupled receptor such that the cell expresses the receptor on its surface and contacting the cell with a potential antagonist in the presence of a labeled form of a known ligand. The ligand can be labeled, e.g., by radioactivity. The amount of labeled ligand bound to the receptors is measured, e.g., by measuring radioactivity of the receptors. If the potential antagonist binds to the receptor as determined by a reduction of labeled ligand which binds to the receptors, the binding of labeled ligand to the receptor is inhibited.

Activation of G-protein coupled receptors normally results in induction of cAMP. Therefore, in an additional specific embodiment of the invention, constructs containing the cAMP responsive element linked to any of a variety of different reporter genes may be introduced into cells expressing the I5E receptor. Such reporter genes may include but is not limited to chloramphenicol acetyltransferase (CAT), luciferase, GUS, growth hormone, or placental alkaline phosphatase (SEAP). Following exposure of the cells to the test compound, the level of reporter gene expression may be quantitated to determine the test compound's ability to regulate receptor activity. Alkaline phosphatase assays are particularly useful in the practice of the invention as the enzyme is secreted from the cell. Therefore, tissue culture supernatant may be assayed for secreted alkaline phosphatase. In addition, alkaline phosphatase activity may be measured by calorimetric, bioluminescent or chemilumenscent assays such as those described in Bronstein, I. et al. (1994, Biotechniques 17: 172–177). Such assays provide a simple, sensitive easily automatable detection system for pharmaceutical screening.

Computer modelling and searching technologies permit identification of compounds, or the improvement of already identified compounds, that can modulate I5E expression or activity. Having identified such a compound or composition, the active sites or regions are identified. Such active sites might typically be ligand binding sites, such as the interaction domains of natural I5E ligand with I5E itself. The active site can be identified using methods known in the art including, for example, from the amino acid sequences of peptides, from the nucleotide sequences of nucleic acids, or from study of complexes of the relevant compound or composition with its natural ligand. In the latter case, chemical or X-ray crystallographic methods can be used to find the active site by finding where on the factor the complexed ligand is found.

Next, the three dimensional geometric structure of the active site is determined. This can be done by known methods, including X-ray crystallography, which can determine a complete molecular structure. On the other hand, solid or liquid phase NMR can be used to determine certain intra-molecular distances. Any other experimental method of structure determination can be used to obtain partial or M complete geometric structures. The geometric structures may be measured with a complexed ligand, natural or artificial, which may increase the accuracy of the active site structure determined.

If an incomplete or insufficiently accurate structure is determined, the methods of computer based numerical modelling can be used to complete the structure or improve its accuracy. Any recognized modelling method may be used, including parameterized models specific to particular biopolymers such as proteins or nucleic acids, molecular dynamics models based on computing molecular motions, statistical mechanics models based on thermal ensembles, or combined models. For most types of models, standard molecular force fields, representing the forces between constituent atoms and groups, are necessary, and can be selected from force fields known in physical chemistry. The incomplete or less accurate experimental structures can serve as constraints on the complete and more accurate structures computed by these modeling methods.

Finally, having determined the structure of the active site, either experimentally, by modeling, or by a combination, candidate modulating compounds can be identified by searching databases containing compounds along with information on their molecular structure. Such a search seeks compounds having structures that match the determined active site structure and that interact with the groups defining the active site. Such a search can be manual, but is preferably computer assisted. These compounds found from this search are potential I5E modulating compounds.

Alternatively, these methods can be used to identify improved modulating compounds from an already known modulating compound or ligand. The composition of the known compound can be modified and the structural effects of modification can be determined using the experimental and computer modelling methods described above applied to the new composition. The altered structure is then compared to the active site structure of the compound to determine if an improved fit or interaction results. In this manner systematic variations in composition, such as by varying side groups, can be quickly evaluated to obtain modified modulating compounds or ligands of improved specificity or activity.

Further experimental and computer modeling methods useful to identify modulating compounds based upon identification of the active sites of natural I5E ligand, I5E, and related transduction and transcription factors will be apparent to those of skill in the art.

Examples of molecular modelling systems are the CHARMm and QUANTA programs (Polygen Corporation, Waltham, Mass.). CHARMm performs the energy minimization and molecular dynamics functions. QUANTA performs the construction, graphic modelling and analysis of molecular structure. QUANTA allows interactive construction, modification, visualization, and analysis of the behavior of molecules with each other.

A number of articles review computer modelling of drugs interactive with specific proteins, such as Rotivinen, et al., 1988, *Acta Pharmaceutical Fennica* 97:159–166; Ripka, *New Scientist* 54–57 (Jun. 16, 1988); McKinaly and Rossmann, 1989, *Annu. Rev. Pharmacol. Toxiciol.* 29:111–122; Perry and Davies, *OSAR: Quantitative Structure-Activity Relationships in Drug Design* pp. 189–193 (Alan R. Liss, Inc. 1989); Lewis and Dean, 1989 *Proc. R. Soc. Lond.* 236:125–140 and 141–162; and, with respect to a model receptor for nucleic acid components, Askew, et al., 1989, *J. Am. Chem. Soc.* 111:1082–1090. Other computer programs that screen and graphically depict chemicals are available from companies such as BioDesign, Inc. (Pasadena, Calif.), Allelix, Inc. (Mississauga, Ontario, Canada), and Hypercube, Inc. (Cambridge, Ontario). Although these are primarily designed for application to drugs specific to particular proteins, they can be adapted to design of drugs specific to regions of DNA or RYA, once that region is identified.

Although described above with reference to design and generation of compounds which could alter binding, one could also screen libraries of known compounds, including natural products or synthetic chemicals, and biologically active materials, including proteins, for compounds which are inhibitors or activators.

Compounds identified via assays such as those described herein may be useful, for example, in elaborating the biological function of the I5E gene product, and for ameliorating disorders arising from the activity of the I5E.

5.4.2. IN VITRO SCREENING ASSAYS FOR COMPOUNDS THAT BIND TO I5E

In vitro systems may be designed to identify compounds capable of interacting with (e.g., binding to) I5E (including, but not limited to, the one or more ECDs or CDs of I5E). Compounds identified may be useful, for example, in modulating the activity of wild type and/or mutant I5E gene products; may be useful in elaborating the biological function of the I5E; may be utilized in screens for identifying compounds that disrupt normal I5E interactions; or may in themselves disrupt such interactions.

The principle of the assays used to identify compounds that bind to the I5E involves preparing a reaction mixture of the I5E and the test compound under conditions and for a time sufficient to allow the two components to interact and bind, thus forming a complex which can be removed and/or detected in the reaction mixture. The I5E species used can vary depending upon the goal of the screening assay. For example, where agonists of the natural ligand are sought, the full length I5E, or a soluble truncated I5E, e.g., in which the one or more of the TM and/or CD domains is deleted from the molecule, a peptide corresponding to one or more of the ECDs or TMs, or a fusion protein containing one or move of the I5E ECDs fused to a protein or polypeptide that affords advantages in the assay system (e.g., labeling, isolation of the resulting complex, etc.) can be utilized. Where compounds that interact with the cytoplasmic domain are sought to be identified, peptides corresponding to the I5E CD and fusion proteins containing the I5E CD can be used.

The screening assays can be conducted in a variety of ways. For example, one method to conduct such an assay would involve anchoring the I5E protein, polypeptide, peptide or fusion protein or the test substance onto a solid phase and detecting I5E/test compound complexes anchored on the solid phase at the end of the reaction. In one embodiment of such a method, the I5E reactant may be anchored onto a solid surface, and the test compound, which is not anchored, may be labeled, either directly or indirectly.

In practice, microtitre plates may conveniently be utilized as the solid phase. The anchored component may be immobilized by non-covalent or covalent attachments. Non-covalent attachment may be accomplished by simply coating the solid surface with a solution of the protein and drying. Alternatively, an immobilized antibody, preferably a monoclonal antibody, specific for the protein to be immobilized may be used to anchor the protein to the solid surface. The surfaces may be prepared in advance and stored.

In order to conduct the assay, the nonimmobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously nonimmobilized component is pre-labeled, the detection of label immobilized on the surface indicates that complexes were formed. Where the previously nonimmobilized component is not pre-labeled, an indirect label can be used to detect complexes anchored on the surface; e.g., using a labeled antibody specific for the previously nonimmobilized component (the antibody, in turn, may be directly labeled or indirectly labeled with a labeled anti-Ig antibody).

Alternatively, a reaction can be conducted in a liquid phase, the reaction products separated from unreacted components, and complexes detected; e.g., using an immobilized antibody specific for I5E protein, polypeptide, peptide or fusion protein or the test compound to anchor any complexes formed in solution, and a labeled antibody specific for the other component of the possible complex to detect anchored complexes.

5.4.3. ASSAYS FOR INTRACELLULAR PROTEINS THAT INTERACT WITH THE I5E

Any method suitable for detecting protein-protein interactions may be employed for identifying transmembrane proteins or intracellular proteins that interact with I5E. Among the traditional methods which may be employed are co-immunoprecipitation, crosslinking and co-purification through gradients or chromatographic columns of cell lysates or proteins obtained from cell lysates and the I5E to identify proteins in the lysate that interact with the I5E. For these assays, the I5E component used can be a full length I5E, a soluble derivative lacking the membrane-anchoring region (e.g., a truncated I5E in which the TM is deleted resulting in a truncated molecule containing the ECD fused to the CD), a peptide corresponding to the CD or a fusion protein containing the CD of I5E. Once isolated, such an intracellular protein can be identified and can, in turn, be used, in conjunction with standard techniques, to identify proteins with which it interacts. For example, at least a portion of the amino acid sequence of an intracellular protein which interacts with the I5E can be ascertained using techniques well known to those of skill in the art, such as via the Edman degradation technique. (See, e.g., Creighton, 1983, "Proteins: Structures and Molecular Principles", W. H. Freeman & Co., N.Y., pp. 34–49). The amino acid sequence obtained may be used as a guide for the generation of oligonucleotide mixtures that can be used to screen for gene sequences encoding such intracellular proteins. Screening may be accomplished, for example, by standard hybridization or PCR techniques. Techniques for the generation of oligonucleotide mixtures and the screening are well-known. (See, e.g., Ausubel, supra., and PCR Protocols: A Guide to Methods and Applications, 1990, Innis, M. et al., eds. Academic Press, Inc., New York).

Additionally, methods may be employed which result in the simultaneous identification of genes which encode the transmembrane or intracellular proteins interacting with I5E. These methods include, for example, probing expression, libraries, in a manner similar to the well known technique of antibody probing of λgt11 libraries, using labeled I5E protein, or an I5E polypeptide, peptide or fusion protein, e.g., an I5E polypeptide or I5E domain fused to a marker (e.g., an enzyme, fluor, luminescent protein, or dye), or an Ig-Fc domain.

One method which detects protein interactions in vivo, the yeast two-hybrid system, is described in detail for illustration only and not by way of limitation. One version of this system has been described (Chien et al., 1991, Proc. Natl. Acad. Sci. USA, 88:9578–9582) and is commercially available from Clontech (Palo Alto, Calif.).

Briefly, utilizing such a system, plasmids are constructed that encode two hybrid proteins: one plasmid consists of nucleotides encoding the DNA-binding domain of a transcription activator protein fused to an I5E nucleotide sequence encoding I5E, an I5E polypeptide, peptide or fusion protein, and the other plasmid consists of nucleotides encoding the transcription activator protein's activation domain fused to a cDNA encoding an unknown protein which has been recombined Into this plasmid as part of a cDNA library. The DNA-binding domain fusion plasmid and the cDNA library are transformed into a strain of the yeast *Saccharomyces cerevisiae* that contains a reporter gene (e.g., HBS or lacZ) whose regulatory region contains the transcription activator's binding site. Either hybrid protein alone cannot activate transcription of the reporter gene: the DNA-binding domain hybrid cannot because it does not provide activation function and the activation domain hybrid cannot because it cannot localize to the activator's binding sites. Interaction of the two hybrid proteins reconstitutes the functional activator protein and results in expression of the reporter gene, which is detected by an assay for the reporter gene product.

The two-hybrid system or related methodology may be used to screen activation domain libraries for proteins that interact with the "bait" gene product. By way of example, and not by way of limitation, I5E may be used as the bait gene product. Total genomic or cDNA sequences are fused to the DNA encoding an activation domain. This library and a plasmid encoding a hybrid of a bait I5E gene product fused to the DNA-binding domain are cotransformed into a yeast reporter strain, and the resulting transformants are screened for those that express the reporter gene. For example, and not by way of limitation, a bait I5E gene sequence, such as the open reading frame of I5E (or a domain of I5E), as depicted in FIGS. 1A–1E can be cloned into a vector such that it is translationally fused to the DNA encoding the DNA-binding domain of the GAL4 protein. These colonies are purified and the library plasmids responsible for reporter gene expression are isolated. DNA sequencing is then used to identify the proteins encoded by the library plasmids.

A cDNA library of the cell line from which proteins that interact with bait I5E gene product are to be detected can be made using methods routinely practiced in the art. According to the particular system described herein, for example, the cDNA fragments can be inserted into a vector such that they are translationally fused to the transcriptional activation domain of GAL4. This library can be co-transformed along with the bait I5E gene-GAL4 fusion plasmid into a yeast strain which contains a lacZ gene driven by a promoter which contains GAL4 activation sequence. A cDNA encoded protein, fused to GAL4 transcriptional activation domain, that interacts with bait I5E gene product will reconstitute an active GAL4 protein and thereby drive expression of the HIS3 gene. Colonies which express HIS3 can be detected by their growth on petri dishes containing semi-solid agar based media lacking histidine. The cDNA can then be purified from these strains, and used to produce and isolate the bait I5E gene-interacting protein using techniques routinely practiced in the art.

5.4.4. ASSAYS FOR COMPOUNDS THAT INTERFERE WITH I5E/INTRACELLULAR OR I5E/TRANSMEMBRANE MACROMOLECULE INTERACTION

The macromolecules that interact with the I5E are referred to, for purposes of this discussion, as "binding partners". These binding partners are likely to be involved in the I5E signal transduction pathway. Therefore, it is desirable to identify compounds that interfere with or disrupt the interaction of such binding partners with natural I5E ligand which may be useful in regulating the activity of the I5E and control disorders associated with I5E activity.

The basic principle of the assay systems used to identify compounds that interfere with the interaction between the I5E and its binding partner or partners involves preparing a reaction mixture containing I5E protein, polypeptide, peptide or fusion protein as described in Sections 5.5.1 and 5.5.2 above, and the binding partner under conditions and for a time sufficient to allow the two to interact and bind, thus forming a complex. In order to test a compound for inhibitory activity, the reaction mixture is prepared in the presence and absence of the test compound. The test compound may be initially included in the reaction mixture, or may be added at a time subsequent to the addition of the I5E moiety and its binding partner. Control reaction mixtures are incubated without the test compound or with a placebo. The formation of any complexes between the I5E moiety and the binding partner is then detected. The formation of a complex in the control reaction, but not in the reaction mixture containing the test compound, indicates that the compound interferes with the interaction of the I5E and the interactive binding partner. Additionally, complex formation within reaction mixtures containing the test compound and normal I5E protein may also be compared to complex formation within reaction mixtures containing the test compound and a mutant I5E. This comparison may be important in those cases wherein it is desirable to identify compounds that disrupt interactions of mutant but not normal I5Es.

The assay for compounds that interfere with the interaction of the I5E and binding partners can be conducted in a heterogeneous or homogeneous format. Heterogeneous assays involve anchoring either the I5E moiety product or the binding partner onto a solid phase and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction by competition can be identified by conducting the reaction in the presence of the test substance; i.e., by adding the test substance to the reaction mixture prior to or simultaneously with the I5E moiety and interactive binding partner. Alternatively, test compounds that disrupt preformed complexes, e.g. compounds with higher binding constants that displace one of the components from the complex, can be tested by adding the test compound to the reaction mixture after complexes have been formed. The various formats are described briefly below.

In a heterogeneous assay system, either the I5E moiety or the interactive binding partner, is anchored onto a solid surface, while the non-anchored species is labeled, either directly or indirectly. In practice, microtitre plates are conveniently utilized. The anchored species may be immobilized by non-covalent or covalent attachments. Non-covalent attachment may be accomplished simply by coating the solid surface with a solution of the I5E gene product or binding partner and drying. Alternatively, an immobilized antibody specific for the species to be anchored may be used to anchor the species to the solid surface. The surfaces may be prepared in advance and stored.

In order to conduct the assay, the partner of the immobilized species is exposed to the coated surface with or without the test compound. After the reaction is complete, unreacted components are removed (e.g., by washing) and any complexes formed will remain immobilized on the solid surface. The detection of complexes anchored on the solid surface can be accomplished in a number of ways. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific for the initially non-immobilized species (the antibody, in turn, may be directly labeled or indirectly labeled with a labeled anti-Ig antibody). Depending upon the order of addition of reaction components, test compounds which inhibit complex formation or which disrupt pre-formed complexes can be detected.

Alternatively, the reaction can be conducted in a liquid phase in the presence or absence of the test compound, the reaction products separated from unreacted components, and complexes detected; e.g., using an immobilized antibody specific for one of the binding components to anchor any complexes formed in solution, and a labeled antibody specific for the other partner to detect anchored complexes. Again, depending upon the order of addition of reactants to the liquid phase, test compounds which inhibit complex or which disrupt preformed complexes can be identified.

In an alternate embodiment of the invention, a homogeneous assay can be used. In this approach, a preformed complex of the I5E moiety and the interactive binding partner is prepared in which either the I5E or its binding partners is labeled, but the signal generated by the label is quenched due to formation of the complex (see, e.g., U.S. Pat. No. 4,109,496 by Rubenstein which utilizes this approach for immunoassays). The addition of a test substance that competes with and displaces one of the species from the preformed complex will result in the generation of a signal above background. In this way, test substances which disrupt I5E/intracellular binding partner interaction can be identified.

In a particular embodiment, an I5E fusion can be prepared for immobilization. For example, the I5E or a peptide fragment, e.g., corresponding to the CD, can be fused to a glutathione-S-transferase (GST) gene using a fusion vector, such as pGEX-5X-1, in such a manner that its binding activity is maintained in the resulting fusion protein. The interactive binding partner can be purified and used to raise a monoclonal antibody, using methods routinely practiced in the art and described above, in Section 5.3. This antibody can be labeled with the radioactive isotope $^{125}$I, for example, by methods routinely practiced in the art. In a heterogeneous assay, e.g., the GST-I5E fusion protein can be anchored to glutathione-agarose beads. The interactive binding partner can then be added in the presence or absence of the test compound in a manner that allows interaction and binding to occur. At the end of the reaction period, unbound material can be washed away, and the labeled monoclonal antibody can be added to the system and allowed to bind to the complexed components. The interaction between the I5E gene product and the interactive binding partner can be detected by measuring the amount of radioactivity that remains associated with the glutathione-agarose beads. A successful inhibition of the interaction by the test compound will result in a decrease in measured radioactivity.

Alternatively, the GST-I5E fusion protein and the interactive binding partner can be mixed together in liquid in the absence of the solid glutathione-agarose beads. The test compound can be added either during or after the species are allowed to interact. This mixture can then be added to the glutathione-agarose beads and unbound material is washed away. Again the extent of inhibition of the I5E/binding partner interaction can be detected by adding the labeled antibody and measuring the radioactivity associated with the beads.

In another embodiment of the invention, these same techniques can be employed using peptide fragments that correspond to the binding domains of the I5E and/or the interactive or binding partner (in cases where the binding partner is a protein), in place of one or both of the full length proteins. Any number of methods routinely practiced in the art can be used to identify and isolate the binding sites. These methods include, but are not limited to, mutagenesis of the gene encoding one of the proteins and screening for disruption of binding in a co-immunoprecipitation assay. Compensating mutations in the gene encoding the second species in the complex can then be selected. Sequence analysis of the genes encoding the respective proteins will reveal the mutations that correspond to the region of the protein involved in interactive binding. Alternatively, one protein can be anchored to a solid surface using methods described above, and allowed to interact with and bind to its labeled binding partner, which has been treated with a proteolytic enzyme, such as trypsin. After washing, a short, labeled peptide comprising the binding domain may remain associated with the solid material, which can be isolated and identified by amino acid sequencing. Also, once the gene coding for the intracellular binding partner is obtained, short gene segments can be engineered to express peptide fragments of the protein, which can then be tested for binding activity and purified or synthesized.

For example, and not by way of limitation, an I5E gene product can be anchored to a solid material as described, above, by making a GST-I5E fusion protein and allowing it to bind to glutathione agarose beads. The interactive binding partner can be labeled with a radioactive isotope, such as $^{35}$S, and cleaved with a proteolytic enzyme such as trypsin. Cleavage products can then be added to the anchored GST-I5E fusion protein and allowed to bind. After washing away unbound peptides, labeled bound material, representing the intracellular binding partner binding domain, can be eluted, purified, and analyzed for amino acid sequence by well-known methods. Peptides so identified can be produced synthetically or fused to appropriate facilitative proteins using recombinant DNA technology.

5.4.5. ASSAYS FOR IDENTIFICATION OF COMPOUNDS THAT AMELIORATE I5E RELATED DISORDERS

Compounds, including but not limited to binding compounds identified via assay techniques such as those described, above, in Sections 5.5.1 through 5.5.3, can be tested for the ability to ameliorate I5E disorder symptoms, including inflammatory, central nervous system and metabolic disorders such as body weight disorders. The assays described above can identify compounds which affect I5E activity (e.g., compounds that bind to the I5E, inhibit binding of the natural ligand, and either activate signal transduction (agonists) or block activation (antagonists), and compounds that bind to the natural ligand of the I5E and neutralize ligand activity); or compounds that affect I5E gene activity (by affecting I5E gene expression, including molecules, e.g., proteins or small organic molecules, that affect or interfere with splicing events so that expression of the full length or the truncated form of the I5E can be modulated). However, it should be noted that the assays described can also identify compounds that modulate I5E signal transduction (e.g., compounds which affect downstream signalling events, such as inhibitors or enhancers of G-protein activities which participate in transducing the signal activated by natural I5E ligand binding to the I5E). The identification and use of such compounds which affect another step in the I5E signal transduction pathway in which the I5E gene and/or I5E gene product is involved and, by affecting this same pathway may modulate the effect of I5E on the development of disorders that are within the scope of the invention. Such compounds can be used as part of a therapeutic method for the treatment of I5E related disorders such as central nervous system inflammatory, immune and metabolic disorders including body weight disorders such as obesity, cachexia and anorexia.

The invention encompasses cell-based and animal model-based assays for the identification of compounds exhibiting such an ability to ameliorate disorder symptoms. Such cell-based assay systems can also be used as the "gold standard" to assay for purity and potency of the natural ligand, natural I5E ligand, including recombinantly or synthetically produced natural I5E ligand and natural I5E ligand mutants.

Cell-based systems can be used to identify compounds which may act to ameliorate gpc-R disorder symptoms. Such cell systems can include, for example, recombinant or non-recombinant cells, such as cell lines, which express the I5E gene. In addition, expression host cells (e.g., COS cells, CHO cells, fibroblasts) genetically engineered to express a functional I5E and to respond to activation by the natural I5E ligand, e.g., as measured by a chemical or phenotypic change, induction of another host cell gene, change in ion flux (e.g., $Ca^{++}$), inositol phosphate levels, tyrosine phosphorylation of host cell proteins, etc., can be used as an end point in the assay.

In utilizing such cell systems, cells may be exposed to a compound suspected of exhibiting an ability to ameliorate I5E disorder symptoms, at a sufficient concentration and for a time sufficient to elicit suppression of disorder symptoms in the exposed cells. After exposure, the cells can be assayed to measure alterations in the expression of the I5E gene, e.g., by assaying cell lysates for I5E mRNA transcripts (e.g., by Northern analysis) or for I5E protein expressed in the cell; compounds which regulate or modulate expression of the I5E gene are good candidates as therapeutics. Still further, the expression and/or activity of components of the signal transduction pathway of which I5E is a part, or the activity of the I5E signal transduction pathway itself can be assayed.

For example, after exposure, the cell lysates can be assayed for activation of phospholipase C of host cell proteins, as compared to lysates derived from unexposed control cells. The ability of a test compound to inhibit activation of phospholipase C in these assay systems indicates that the test compound inhibits signal transduction initiated by I5E activation. The cell lysates can be readily assayed for phosphatiylinositol turnover as measured by inositol phosphate (IP) accumulation in cells.

In addition, animal-based I5E based disorder systems, which may include, may be used to identify compounds capable of ameliorating disorder-like symptoms. Such animal models may be used as test substrates for the identification of drugs, pharmaceuticals, therapies and interventions which may be effective in treating such disorders. For example, animal models may be exposed to a compound, suspected of exhibiting an ability to ameliorate disorder symptoms, at a sufficient concentration and for a time sufficient to elicit such an amelioration of body symptoms in the exposed animals. The response of the animals to the exposure may be monitored by assessing the reversal of I5E based disorders such as inflammatory, central nervous system and metabolic disorders such as body weight disorders. With regard to intervention, any treatments which reverse any aspect of disorder-like symptoms should be considered as candidates for human therapeutic intervention. Dosages of test agents may be determined by deriving dose-response curves, as discussed in Section 5.7.1, below.

5.5. THE TREATMENT OF I5E BASED DISORDERS

The invention encompasses methods and compositions treating I5E based disorders, including but not limited to immune disorders such as inflammatory disorders, immune and central nervous system disorders. The invention also encompasses the treatment of metabolic disorders such as body weight disorders, including but not limited to, obesity, cachexia and anorexia.

Symptoms of certain I5E based disorders may be ameliorated by decreasing the level of I5E gene expression, and/or I5E gene activity, and/or downregulating activity of the I5E pathway (e.g., by targeting downstream signalling events). Different approaches are discussed below.

5.5.1. INHIBITION OF I5E EXPRESSION OR I5E ACTIVITY

Any method which neutralizes natural I5E ligand or inhibits expression of the I5E gene (either transcription or translation) can be used to treat I5E based disorders. Such approaches can be used to treat various maladies such as inflammatory disorders, immune central nervous system disorders or metabolic disorders.

For example, the administration of soluble peptides, proteins, fusion proteins, or antibodies (including anti-idiotypic antibodies) that bind to and "neutralize" the natural ligand for the I5E, can be used to regulate the I5E. To this end, peptides corresponding to the ECD of I5E, soluble deletion mutants of I5E (e.g., ΔTMI5E mutants), or either of these I5E domains or mutants fused to another polypeptide (e.g., an IgFc polypeptide) can be utilized. Alternatively, anti-idiotypic antibodies or Fab fragments of antiidiotypic antibodies that mimic the I5E ECD and neutralize natural I5E ligand can be used (see Section 5.3, supra). Such I5E peptides, proteins, fusion proteins, anti-idiotypic antibodies or Fibs are administered to a subject in amounts sufficient to neutralize natural I5E ligand and to inhibit the activity of the I5E.

Fusion of the I5E, the I5E one or more of the ECDs or the ΔTMI5E to an IgFc polypeptide should not only increase the stability of the preparation, but will increase the half-life and activity of the I5E-Ig fusion protein in vivo. The Fc region of the Ig portion of the fusion protein may be further modified to reduce immunoglobulin effector function.

In an alternative embodiment for neutralizing circulating natural I5E ligand, cells that are genetically engineered to express such soluble or secreted forms of I5E may be administered to a patient, whereupon they will serve as "bioreactors" in vivo to provide a continuous supply of the natural I5E ligand neutralizing protein. Such cells may be obtained from the patient or an MHC compatible donor and can include, but are not limited to fibroblasts, blood cells (e.g., lymphocytes), adipocytes, muscle cells, endothelial cells etc. The cells are genetically engineered in vitro using recombinant DNA techniques to introduce the coding sequence for one or more of the I5E ECDs, ΔTMI5E, or for I5E-Ig fusion protein (e.g., I5E-, ECD- or ΔTMI5E-IgFc fusion proteins) into the cells, e.g., by transduction (using viral vectors, and preferably vectors that integrate the transgene into the cell genome) or transfection procedures, including but not limited to the use of plasmids, cosmids, YACs, electroporation, liposomes, etc. The I5E coding sequence can be placed under the control of a strong constitutive or inducible promoter or promoter/enhancer to achieve expression and secretion of the I5E peptide or fusion protein. The engineered cells which express and secrete the desired I5E product can be introduced into the patient systemically, e.g., in the circulation, or intraperitoneally. Alternatively, the cells can be incorporated into a matrix and implanted in the body, e.g., genetically engineered fibroblasts can be implanted as part of a skin graft; genetically engineered endothelial cells can be implanted as part of a vascular graft. (See, for example, Anderson et al. U.S. Pat. No. 5,399,349; and Mulligan & Wilson, U.S. Pat. No. 5,460,959 each of which is incorporated by reference herein in its entirety).

When the cells to be administered are non-autologous cells, they can be administered using well known techniques which prevent the development of a host immune response against the introduced cells. For example, the cells may be introduced in an encapsulated form which, while allowing for an exchange of components with the immediate extracellular environment, does not allow the introduced cells to be recognized by the host immune system.

In an alternate embodiment, therapies can be designed to reduce the level of endogenous I5E gene expression, e.g., using antisense or ribozyme approaches to inhibit or prevent translation of I5E mRNA transcripts; triple helix approaches to inhibit transcription of the I5E gene; or targeted homologous recombination to inactivate or "knock out" the I5E gene or its endogenous promoter. Alternatively, the antisense, ribozyme or DNA constructs described herein could be administered directly to a site containing the target cells; e.g., cells expressing the I5E.

Antisense approaches involve the design of oligonucleotides (either DNA or RNA) that are complementary to I5E mRNA. The antisense oligonucleotides will bind to the complementary I5E mRNA transcripts and prevent translation. Absolute complementarily, although preferred, is not required. A sequence "complementary" to a portion of an RNA, as referred to herein, means a sequence having sufficient complementarily to be able to hybridize with the RNA, forming a stable duplex; in the case of double-stranded antisense nucleic acids, a single strand of the duplex DNA may thus be tested, or triplex formation may be assayed. The ability to hybridize will depend on both the degree of complementarily and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex.

Oligonucleotides that are complementary to the 5' end of the message, e.g., the 5' untranslated sequence up to and including the AUG initiation codon, should work most efficiently at inhibiting translation. However, sequences complementary to the 3' untranslated sequences of mRNAs have recently shown to be effective at inhibiting translation of mRNAs as well. See generally, Wagner, R., 1994, Nature 372:333–335. Thus, oligonucleotides complementary to either the 5'- or 3'- non- translated, non-coding regions of the I5E shown in FIGS. 1A–1E could be used in an antisense approach to inhibit translation of endogenous I5E mRNA. Oligonucleotides complementary to the 5' untranslated region of the mRNA should include the complement of the AUG start codon. Antisense oligonucleotides complementary to mRNA coding regions are less efficient inhibitors of translation but could be used in accordance with the invention. Whether designed to hybridize to the 5'-, 3'- or coding region of I5E mRNA, antisense nucleic acids should be at least six nucleotides in length, and are preferably oligonucleotides ranging from 6 to about 50 nucleotides in length. In specific aspects the oligonucleotide is at least 10 nucleotides, at least 17 nucleotides, at least 25 nucleotides or at least 50 nucleotides.

Regardless of the choice of target sequence, it is preferred that in vitro studies are first performed to quantitate the ability of the antisense oligonucleotide to inhibit gene expression. It is preferred that these studies utilize controls that distinguish between antisense gene inhibition and non-specific biological effects of oligonucleotides. It is also preferred that these studies compare levels of the target RNA or protein with that of an internal control RNA or protein. Additionally, it is envisioned that results obtained using the antisense oligonucleotide are compared with those obtained using a control oligonucleotide. It is preferred that the control oligonucleotide is of approximately the same length as the test oligonucleotide and that the nucleotide sequence of the oligonucleotide differs from the antisense sequence no more than is necessary to prevent specific hybridization to the target sequence.

The oligonucleotides can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (see, e.g., Letsinger et al., 1989, Proc. Natl. Acad. Sci. U.S.A. 86:6553–6556; Lemaitre et al., 1987, Proc. Natl. Acad. Sci. 84:648–652; PCT Publication No. WO88/09810, published Dec. 15, 1988) or the blood-brain barrier (see, e.g., PCT Publication No. WO89/10134, published Apr. 25, 1988), hybridization-triggered cleavage agents. (See, e.g., Krol et al., 1988, BioTechniques 6:958–976) or intercalating agents. (See, e.g., Zon, 1988, Pharm. Res. 5:539–549). To this end, the oligonucleotide may be conjugated to another molecule, e.g., a peptide, hybridization triggered cross-linking agent, transport agent, hybridization-triggered cleavage agent, etc.

The antisense oligonucleotide may comprise at least one modified base moiety which is selected from the group including but not limited to 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

The antisense oligonucleotide may also comprise at least one modified sugar moiety selected from the group including but not limited to arabinose, 2-fluoroarabinose, xylulose, and hexose.

In yet another embodiment, the antisense oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an α-anomeric oligonucleotide. An α-anomeric oligonucleotide forms specific double-stranded hybrids with complementary RNA in which, contrary to the usual β-units, the strands run parallel to each other (Gautier et al., 1987, Nucl. Acids Res. 15:6625–6641). The oligonucleotide is a 2'-O-methylribonucleotide (Inoue et al., 1987, Nucl. Acids Res. 15:6131–6148), or a chimeric RNA-DNA analogue (Inoue et al., 1987, FEBS Lett. 215:327–330).

Oligonucleotides of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al. (1988, Nucl. Acids Res. 16:3209), methylphosphonate oligonucleotides can be prepared by use of controlled pore glass polymer supports (Sarin et al., 1988, Proc. Natl. Acad. Sci. U.S.A. 85:7448–7451), etc.

While antisense nucleotides complementary to the I5E coding region sequence could be used, those complementary to the transcribed untranslated region are most preferred. For example, antisense oligonucleotides having the following sequences can be utilized in accordance with the invention:

The antisense molecules should be delivered to cells which express the I5E in vivo. A number of methods have been developed for delivering antisense DNA or RNA to cells; e.g., antisense molecules can be injected directly into the tissue site, or modified antisense molecules, designed to target the desired cells (e.g., antisense linked to peptides or antibodies that specifically bind receptors or antigens expressed on the target cell surface) can be administered systemically.

However, it is often difficult to achieve intracellular concentrations of the antisense sufficient to suppress translation of endogenous mRNAs. Therefore a preferred approach utilizes a recombinant DNA construct in which the antisense oligonucleotide is placed under the control of a strong pol III or pol II promoter. The use of such a construct to transfect target cells in the patient will result in the transcription of sufficient amounts of single stranded RNAs that will form complementary base pairs with the endogenous I5E transcripts and thereby prevent translation of the I5E mRNA. For example, a vector can be introduced in vivo such that it is taken up by a cell and directs the transcription of an antisense RNA. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequence encoding the antisense RNA can be by any promoter known in the art to act in mammalian, preferably human cells. Such promoters can be inducible or constitutive. Such promoters include but are not limited to: the SV40 early promoter region (Bernoist and Chambon, 1981, Nature 290:304–310), the promoter contained in the 3' long terminal repeat of Rous sarcoma virus (Yamamoto et al., 1980, Cell 22:787–797), the herpes thymidine kinase promoter (Wagner et al., 1981, Proc. Natl. Acad. Sci. U.S.A. 78:1441–1445), the regulatory sequences of the metallothionein gene (Brinster et al., 1982, Nature 296:39–42), etc. Any type of plasmid, cosmid, YAC or viral vector can be used to prepare the recombinant DNA construct which can be introduced directly into the tissue site; e.g., tissue in which I5E is expressed. Alternatively, viral vectors can be used which selectively infect the desired tissue; (e.g., for brain, herpesvirus vectors may be used), in which case administration may be accomplished by another route (e.g., systemically).

Ribozyme molecules designed to catalytically cleave I5E mRNA transcripts can also be used to prevent translation of I5E mRNA and expression of I5E. (See, e.g., PCT International Publication WO90/11364, published Oct. 4, 1990; Sarver et al., 1990, Science 247:1222–1225). While ribozymes that cleave mRNA at site specific recognition sequences can be used to destroy I5E mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach, 1988, Nature, 334:585–591. There are hundreds of potential hammerhead ribozyme cleavage sites within the nucleotide sequence of human I5E cDNA. Preferably the ribozyme is engineered so that the cleavage recognition site is located near the 5' end of the I5E mRNA; i.e., to increase efficiency and minimize the intracellular accumulation of non-functional mRNA transcripts.

The ribozymes of the present invention also include RNA endoribonucleases (hereinafter "Cech-type ribozymes") such as the one which occurs naturally in Tetrahymena Thermophila (known as the IVS, or L-19 IVS RNA) and which has been extensively described by Thomas Cech and collaborators (Zaug, et al., 1984, Science, 224:574–578; Zaug and Cech, 1986, Science, 231:470–475; Zaug, et al., 1986, Nature, 324:429–433; published International patent application No. WO 88/04300 by University Patents Inc.; Been and Cech, 1986, Cell, 47:207–216). The Cech-type ribozymes have an eight base pair active site which hybridizes to a target RNA sequence whereafter cleavage of the target RNA takes place. The invention encompasses those Cech-type ribozymes which target eight base-pair active site sequences that are present in I5E.

As in the antisense approach, the ribozymes can be composed of modified oligonucleotides (e.g. for improved stability, targeting, etc.) and should be delivered to cells which express the I5E in vivo. A preferred method of delivery involves using a DNA construct "encoding" the ribozyme under the control of a strong constitutive pol III or pol II promoter, so that transfected cells will produce sufficient quantities of the ribozyme to destroy endogenous I5E messages and inhibit translation. Because ribozymes unlike antisense molecules, are catalytic, a lower intracellular concentration is required for efficiency.

Endogenous I5E gene expression can also be reduced by inactivating or "knocking out" the I5E gene or its promoter using targeted homologous recombination. (E.g., see Smithies et al., 1985, Nature 317:230–234; Thomas & Capecchi, 1987, Cell 51:503–512; Thompson et al., 1989 Cell 5:313–321; each of which is incorporated by reference herein in its entirety). For example, a mutant, non-functional I5E (or a completely unrelated DNA sequence) flanked by DNA homologous to the endogenous I5E gene (either the coding regions or regulatory regions of the I5E gene) can be used, with or without a selectable marker and/or a negative selectable marker, to transfect cells that express I5E in vivo. Insertion of the DNA construct, via targeted homologous recombination, results in inactivation of the I5E gene. Such approaches are particularly suited in the agricultural field where modifications to ES (embryonic stem) cells can be used to generate animal offspring with an inactive I5E (e.g., see Thomas & Capecchi 1987 and Thompson 1989, supra). However this approach can be adapted for use in humans provided the recombinant DNA constructs are directly administered or targeted to the required site in vivo using appropriate viral vectors, e.g., herpes virus vectors for delivery to brain tissue.

Alternatively, endogenous I5E gene expression can be reduced by targeting deoxyribonucleotide sequences complementary to the regulatory region of the I5E gene (i.e., the I5E promoter and/or enhancers) to form triple helical structures that prevent transcription of the I5E gene in target cells in the body. (See generally, Helene, C. 1991, Anticancer Drug Des., 6(6):569–84; Helene, C., et al., 1992, Ann, N.Y. Accad. Sci., 660:27–36; and Maher, L. J., 1992, Bioassays 14(12):807–15).

5.5.2. RESTORATION OR INCREASE IN I5E EXPRESSION OR ACTIVITY

With respect to an increase in the level of normal I5E gene expression and/or I5E gene product activity, I5E nucleic acid sequences can be utilized for the treatment of disorders resulting from a disfunctional I5E, including inflammatory, central nervous system. Where the cause of a given disorder is a defective I5E, treatment can be administered, for example, in the form of gene replacement therapy. Specifically, one or more copies of a normal I5E gene or a portion of the I5E gene that directs the production of an I5E gene product exhibiting normal function, may be inserted into the appropriate cells within a patient or animal subject, using vectors which include, but are not limited to adenovirus, adeno-associated virus, retrovirus and herpes virus vectors, in addition to other particles that introduce DNA into cells, such as liposomes.

Targeted homologous recombination can be utilized to correct the defective endogenous I5E gene in the appropriate tissue. In animals, targeted homologous recombination can be used to correct the defect in ES cells in order to generate offspring with a corrected trait.

Additional methods which may be utilized to increase the overall level of I5E gene expression and/or I5E activity include the introduction of appropriate I5E-expressing cells, preferably autologous cells, into a patient at positions and in numbers which are sufficient to ameliorate the symptoms of I5E disorders. Such cells may be either recombinant or non-recombinant. Among the cells which can be administered to increase the overall level of I5E gene expression in a patient are normal cells. The cells can be administered at the anatomical site in the brain, or as part of a tissue graft located at a different site in the body. Such cell-based gene therapy techniques are well known to those skilled in the art, see, e.g., Anderson, et al., U.S. Pat. No. 5,399,349; Mulligan & Wilson, U.S. Pat. No. 5,460,959.

Finally, compounds, identified in the assays described above, that stimulate or enhance the signal transduced by activated I5E, e.g., by activating downstream signalling proteins in the I5E cascade and thereby by-passing the defective I5E, can be used to treat I5E based disorders. The formulation and mode of administration will depend upon the physico-chemical properties of the compound. The administration should include known techniques that allow for a crossing of the blood-brain barrier.

5.6. PHARMACEUTICAL PREPARATIONS AND METHODS OF ADMINISTRATION

The compounds that are determined to affect I5E gene expression or I5E activity can be administered to a patient at therapeutically effective doses to treat or ameliorate I5E based disorders including inflammatory, central nervous system and metabolic disorders. A therapeutically effective dose refers to that amount of the compound sufficient to result in amelioration of symptoms of the various disorders.

5.6.1. EFFECTIVE DOSE

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

5.6.2. FORMULATIONS AND USE

Pharmaceutical compositions for use in accordance with the present invention may be formulated in conventional manner using one or more physiologically acceptable carriers or excipients.

Thus, the compounds and their physiologically acceptable salts and solvates may be formulated for administration by inhalation or insufflation (either through the mouth or the nose) or oral, buccal, parenteral or rectal administration.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g, lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound.

For buccal administration the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

5.7. DIAGNOSIS DISORDERS ASSOCIATED WITH ABNORMALITIES IN I5E

A variety of methods can be employed for the diagnostic and prognostic evaluation of immune or central nervous system disorders, or metabolic disorders such as body weight disorders, including and for the identification of subjects having a predisposition to such disorders.

Such methods may, for example, utilize reagents such as the I5E nucleotide sequences described in Section 5.1, and I5E antibodies, as described, in Section 5.3. Specifically, such reagents may be used, for example, for: (1) the detection of the presence of I5E gene mutations, or the detection of either over- or under-expression of I5E mRNA relative to the non-disorder state; (2) the detection of either an over- or an under-abundance of I5E gene product relative to the non-disorder state; and (3) the detection of perturbations or abnormalities in the signal transduction pathway mediated by I5E.

The methods described herein may be performed, for example, by utilizing pre-packaged diagnostic kits comprising at least one specific I5E nucleotide sequence or I5E antibody reagent described herein, which may be conveniently used, e.g., in clinical settings, to diagnose patients exhibiting disorder abnormalities.

For the detection of I5E mutations, any nucleated cell can be used as a starting source for genomic nucleic acid. For the detection of I5E gene expression or I5E gene products, any cell type or tissue in which the I5E gene is expressed, may be utilized.

Nucleic acid-based detection techniques are described, below, in Section 5.7.1. Peptide detection techniques are described, below, in Section 5.7.2.

5.7.1. DETECTION OF THE I5E GENE AND TRANSCRIPTS

Mutations within the I5E gene can be detected by utilizing a number of techniques. Nucleic acid from any nucleated cell can be used as the starting point for such assay techniques, and may be isolated according to standard nucleic acid preparation procedures which are well known to those of skill in the art.

DNA may be used in hybridization or amplification assays of biological samples to detect abnormalities involving I5E gene structure, including point mutations, insertions, deletions and chromosomal rearrangements. Such assays may include, but are not limited to, Southern analyses, single stranded conformational polymorphism analyses (SSCP), and PCR analyses.

Such diagnostic methods for the detection of I5E gene-specific mutations can involve for example, contacting and incubating nucleic acids including recombinant DNA molecules, cloned genes or degenerate variants thereof, obtained from a sample, e.g., derived from a patient sample or other appropriate cellular source, with one or more labeled nucleic acid reagents including recombinant DNA molecules, cloned genes or degenerate variants thereof, as described in Section 5.1, under conditions favorable for the specific annealing of these reagents to their complementary sequences within the I5E gene. Preferably, the lengths of these nucleic acid reagents are at least 15 to 30 nucleotides. After incubation, all non-annealed nucleic acids are removed from the nucleic acid:I5E molecule hybrid. The presence of nucleic acids which have hybridized, if any such molecules exist, is then detected. Using such a detection scheme, the nucleic acid from the cell type or tissue of interest can be immobilized, for example, to a solid support such as a membrane, or a plastic surface such as that on a microtitre plate or polystyrene beads. In this case, after incubation, non-annealed, labeled nucleic acid reagents of the type described in Section 5.1 are easily removed. Detection of the remaining, annealed, labeled I5E nucleic acid reagents is accomplished using standard techniques well-known to those in the art. The I5E gene sequences to which the nucleic acid reagents have annealed can be compared to the annealing pattern expected from a normal I5E gene sequence in order to determine whether an I5E gene mutation is present.

Alternative diagnostic methods for the detection of I5E gene specific nucleic acid molecules, in patient samples or other appropriate cell sources, may involve their amplification, e.g., by PCR (the experimental embodiment set forth in Mullis, K. B., 1987, U.S. Pat. No. 4,683,202), followed by the detection of the amplified molecules using techniques well known to those of skill in the art. The resulting amplified sequences can be compared to those which would be expected if the nucleic acid being amplified contained only normal copies of the I5E gene in order to determine whether an I5E gene mutation exists.

Additionally, well-known genotyping techniques can be performed to identify individuals carrying I5E gene mutations. Such techniques include, for example, the use of restriction fragment length polymorphisms (RFLPs), which involve sequence variations in one of the recognition sites for the specific restriction enzyme used.

Additionally, improved methods for analyzing DNA polymorphisms which can be utilized for the identification of I5E gene mutations have been described which capitalize on the presence of variable numbers of short, tandemly repeated DNA sequences between the restriction enzyme sites. For example, Weber (U.S. Pat. No. 5,075,217, which is incorporated herein by reference in its entirety) describes a DNA marker based on length polymorphisms in blocks of (dC-dA)n-(dG-dT)n short tandem repeats. The average separation of (dC-dA)n-(dG-dT)n blocks is estimated to be 30,000–60,000 bp. Markers which are so closely spaced exhibit a high frequency co-inheritance, and are extremely useful in the identification of genetic mutations, such as, for example, mutations within the I5E gene, and the diagnosis of diseases and disorders related to I5E mutations.

Also, Caskey et al. (U.S. Pat. No. 5,364,759, which is incorporated herein by reference in its entirety) describe a DNA profiling assay for detecting short tri and tetra nucleotide repeat sequences. The process includes extracting the DNA of interest, such as the I5E gene, amplifying the extracted DNA, and labelling the repeat sequences to form a genotypic map of the individual's DNA.

The level of I5E gene expression can also be assayed by detecting and measuring I5E transcription. For example, RNA from a cell type or tissue known, or suspected to express the I5E gene may be isolated and tested utilizing hybridization or PCR techniques such as are described, above. The isolated cells can be derived from cell culture or from a patient. The analysis of cells taken from culture may be a necessary step in the assessment of cells to be used as part of a cell-based gene therapy technique or, alternatively, to test the effect of compounds on the expression of the I5E gene. Such analyses may reveal both quantitative and qualitative aspects of the expression pattern of the I5E gene, including activation or inactivation of I5E gene expression.

In one embodiment of such a detection scheme, cDNAs are synthesized from the RNAs of interest (e.g., by reverse transcription of the RNA molecule into cDNA). A sequence within the cDNA is then used as the template for a nucleic acid amplification reaction, such as a PCR amplification reaction, or the like. The nucleic acid reagents used as synthesis initiation reagents (e.g., primers) in the reverse transcription and nucleic acid amplification steps of this method are chosen from among the I5E nucleic acid reagents described in Section 5.1. The preferred lengths of such nucleic acid reagents are at least 9–30 nucleotides. For detection of the amplified product, the nucleic acid amplification may be performed using radioactively or non-radioactively labeled nucleotides. Alternatively, enough amplified product may be made such that the product may be visualized by standard ethidium bromide staining or by utilizing any other suitable nucleic acid staining method.

Additionally, it is possible to perform such I5E gene expression assays "in situ", i.e., directly upon tissue sections (fixed and/or frozen) of patient tissue obtained from biopsies or resections, such that no nucleic acid purification is necessary. Nucleic acid reagents such as those described in Section 5.1 may be used as probes and/or primers for such in situ procedures (See, for example, Nuovo, G. J., 1992, "PCR In Situ Hybridization: Protocols And Applications", Raven Press, NY).

Alternatively, if a sufficient quantity of the appropriate cells can be obtained, standard Northern analysis can be performed to determine the level of mRNA expression of the I5E gene.

5.7.2. DETECTION OF THE I5E GENE PRODUCTS

Antibodies directed against wild type or mutant I5E gene products or conserved variants or peptide fragments thereof, which are discussed, above, in Section 5.3, may also be used as I5E based disorder diagnostics and prognostics, as described herein. Such diagnostic methods, may be used to detect abnormalities in the level of I5E gene expression, or abnormalities in the structure and/or temporal, tissue, cellular, or subcellular location of the I5E, and may be performed in vivo or in vitro, such as, for example, on biopsy tissue.

For example, antibodies directed to epitopes of the I5E ECD can be used in vivo to detect the pattern and level of expression of the I5E in the body. Such antibodies can be labeled, e.g., with a radio-opaque or other appropriate compound and injected into a subject in order to visualize binding to the I5E expressed in the body using methods such as X-rays, CAT-scans, or MRI. Labeled antibody fragments, e.g., the Fab or single chain antibody comprising the smallest portion of the antigen binding region, are preferred for this purpose to promote crossing the blood-brain barrier.

Additionally, any I5E fusion protein or I5E conjugated protein whose presence can be detected, can be administered. For example, I5E fusion or conjugated proteins labeled with a radio-opaque or other appropriate compound can be administered and visualized in vivo, as discussed, above for labeled antibodies.

Alternatively, immunoassays or fusion protein detection assays, as described above, can be utilized on biopsy and autopsy samples in vitro to permit assessment of the expression pattern of the I5E. Such assays are not confined to the use of antibodies that define one of the I5E ECDs, but can include the use of antibodies directed to epitopes of any of the domains of the I5E, e.g., the ECDs, the TM domains and/or CD. The use of each or all of these labeled antibodies will yield useful information regarding translation and intracellular transport of the I5E to the cell surface, and can identify defects in processing.

The tissue or cell type to be analyzed will generally include those which are known, or suspected, to express the I5E gene. The protein isolation methods employed herein may, for example, be such as those described in Harlow and Lane (Harlow, E. and Lane, D., 1988, "Antibodies: A Laboratory Manual", Cold Spring Harbor Laboratory Press, Cold Spring Harbor, New York), which is incorporated herein by reference in its entirety. The isolated cells can be derived from cell culture or from a patient. The analysis of cells taken from culture may be a necessary step in the assessment of cells that could be used as part of a cell-based gene therapy technique or, alternatively, to test the effect of compounds on the expression of the I5E gene.

For example, antibodies, or fragments of antibodies, such as those described, above, in Section 5.3, useful in the present invention may be used to quantitatively or qualitatively detect the presence of I5E gene products or conserved variants or peptide fragments thereof. This can be accomplished, for example, by immunofluorescence techniques employing a fluorescently labeled antibody (see below, this Section) coupled with light microscopic, flow cytometric, or fluorimetric detection. Such techniques are especially preferred if such I5E gene products are expressed on the cell surface.

The antibodies (or fragments thereof) or natural I5E ligand fusion or conjugated proteins useful in the present invention may, additionally, be employed histologically, as in immunofluorescence, immunoelectron microscopy or non-immuno assays, for in situ detection of I5E gene products or conserved variants or peptide fragments thereof, or for natural I5E ligand binding (in the case of labeled natural I5E ligand fusion protein).

In situ detection may be accomplished by removing a histological specimen from a patient, and applying thereto a labeled antibody or fusion protein of the present invention. The antibody (or fragment) or fusion protein is preferably applied by overlaying the labeled antibody (or fragment) onto a biological sample. Through the use of such a procedure, it is possible to determine not only the presence of the I5E gene product, or conserved variants or peptide fragments, or natural I5E ligand binding, but also its distribution in the examined tissue. Using the present invention, those of ordinary skill will readily perceive that any of a wide variety of histological methods (such as staining procedures) can be modified in order to achieve such in situ detection.

Immunoassays and non-immunoassays for I5E gene products or conserved variants or peptide fragments thereof will typically comprise incubating a sample, such as a biological fluid, a tissue extract, freshly harvested cells, or lysates of cells which have been incubated in cell culture, in the presence of a detectably labeled antibody capable of identifying I5E gene products or conserved variants or peptide fragments thereof, and detecting the bound antibody by any of a number of techniques well-known in the art.

The biological sample may be brought in contact with and immobilized onto a solid phase support or carrier such as nitrocellulose, or other solid support which is capable of immobilizing cells, cell particles or soluble proteins. The support may then be washed with suitable buffers followed by treatment with the detectably labeled I5E antibody or natural I5E ligand fusion protein. The solid phase support may then be washed with the buffer a second time to remove unbound antibody or fusion protein. The amount of bound label on solid support may then be detected by conventional means.

By "solid phase support or carrier" is intended any support capable of binding an antigen or an antibody. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads. Those skilled in the art will know many other suitable carriers for binding antibody or antigen, or will be able to ascertain the same by use of routine experimentation.

The binding activity of a given lot of I5E antibody or natural I5E ligand fusion protein may be determined according to well known methods. Those skilled in the art will be able to determine operative and optimal assay conditions for each determination by employing routine experimentation.

With respect to antibodies, one of the ways in which the I5E antibody can be detectably labeled is by linking the same to an enzyme and use in an enzyme immunoassay (EIA) (Voller, A., "The Enzyme Linked Immunosorbent Assay (ELISA)", 1978, Diagnostic Horizons 2:1–7, Microbiological Associates Quarterly Publication, Walkersville, Md.); Voller, A. et al., 1978, J. Clin. Pathol. 31:507–520; Butler, J. E., 1981, Meth. Enzymol. 73:482–523; Maggio, E. (ed.), 1980, Enzyme Immunoassay, CRC Press, Boca Raton, Fla.,; Ishikawa, E. et al., (eds.), 1981, Enzyme Immunoassay, Kgaku Shoin, Tokyo). The enzyme which is bound to the antibody will react with an appropriate substrate, preferably a chromogenic substrate, in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by colorimetric methods which employ a chromogenic substrate for the enzyme, Detection may also be accomplished by visual comparison of the extent of enzymatic reaction of a substrate in comparison with similarly prepared standards.

Detection may also be accomplished using any of a variety of other immunoassays. For example, by radioactively labeling the antibodies or antibody fragments, it is possible to detect I5E through the use of a radioimmunoassay (RIA) (see, for example, Weintraub, B., Principles of Radioimmunoassays, Seventh Training Course on Radioligand Assay Techniques, The Endocrine Society, March, 1986, which is incorporated by reference herein). The radioactive isotope can be detected by such means as the use of a gamma counter or a scintillation counter or by autoradiography.

It is also possible to label the antibody with a fluorescent compound. When the fluorescently labeled antibody is exposed to light of the proper wave length, its presence can then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine.

The antibody can also be detectably labeled using fluorescence emitting metals such as $^{152}$Eu, or others of the lanthanide series. These metals can be attached to the antibody using such metal chelating groups as diethylenetriaminepentacetic acid (DTPA) or ethylenediaminetetraacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in, which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

6. EXAMPLE

ISOLATION AND CHARACTERIZATION OF A NOVEL G-PROTEIN COUPLED RECEPTOR

The following subsection describes the isolation and characterization of a novel human G-protein coupled receptor referred to as I5E. The deduced amino acid sequence of the novel receptor molecule indicates homology with the neuropeptide Y receptor (NPY-2).

6.1. MATERIALS AND METHODS

A sheared BAC library was constructed from murine chromosome 2. The average fragment size was 2 kb. Fragments were cloned into the vector pJCP2 for nucleotide sequencing. Approximately 800 clones were sequenced with vector primers in order to generate a 4.6 fold sequence coverage of the BAC.

Clones were sequenced by standard automated fluorescent dideoxynucleotide sequencing using dye primer chemistry (Applied Biosystems, Inc., Forster City, Calif.) on Applied Biosystems 373 and 377 seqenators. The DNA sequences were screened to eliminate bacterial, ribosomal and mitochondrial contaminants. Sequence artifacts were also eliminated, such as vector and repetitive element sequences.

The following primers were used to generate a 877 bp fragment which was used to screen a human fetal brain cDNA library:

5'-TGCTGCTTAAACCTGGGTCGG-3' (SEQ ID NO:3)
5'-GGTGTGTGATTTACTGAGTACCG-3' (SEQ ID NO:4)

Upon amplification the probe was gel purified and radiolabelled according to standard protocols. Screening was performed on a human fetal brain cDNA library. Hybridization was performed overnight at 50° C. A final washing stringency of 1× SSC/1% SDS at 50° C. was achieved. Autoradiography was performed overnight.

Standard DNA sequencing techniques were utilized for the sequencing and identification of the resulting human I5E gene. The same computer programs as above were used to find identity with the NPY-2 receptor.

6.2. RESULTS

The human I5E sequences were searched against a copy of the GenBank nucleotide database using the BLASTIN program (BLASTIN 1.3MP; Altschul et al., 1990, J. Mol. Biol. 215:403) and a non-redundant protein database with the BLASTX program (BLASTX 1.3MP; Altschul et al., supra). Assembly of overlapping clones into contigs resulted in the identification of one exon which contained the gene of interest. The gene as shown in FIGS. 1A–1E, contains an open reading frame of 385 amino acids. The 385 amino acids in the open reading frame were predicted to encode a G-protein coupled receptor using the method of Von Heijne (1990, J. Membrane Biol. 115:195). The protein shows 24% homology with the neuropeptide Y receptor (NPY-2) at the amino acid level. The predicted transmembrane domains span from about amino acids 54–77, 90–112, 140–162, 171–191, 224–244, 274–296 and 312–336.

7. EXAMPLE

EXPRESSION OF RECOMBINANT I5E IN COS CELLS

The expression plasmid, I5E HA is derived from the vector pcDNAI/Amp (Invitrogen) and contains the following elements: (i) an SV40 origin of replication; (ii) the ampicillin resistance gene; (iii) the E.coli replication origin; (iv) CMV promoter followed by a polylinker region; and an SV40 intron and polyadenylation site. A DNA fragment encoding the entire human I5E precursor with a HA tag fused in frame at its 3' end is cloned into the polylinker region of the pcDNAI/AMP vector, therefore, placing the expression of the human IE5 protein directly under the control of the CMV promoter. The HA tag corresponds to an epitope derived from the influenza hemagglutinin protein as previously described (I. Wilson, H. Niman, R. Heighten, A. Cherenson, M. Connolly, and R. Lerner, 1984, Cell 37:767). The linkage of the HA tag to the I5E protein allows easy detection of the recombinant protein with an antibody that recognizes the HA epitope.

The plasmid construction strategy is described as follows:

The DNA sequence encoding for I5E, is constructed by PCR using two primers: containing complementary sequences to an XhoI site, translation stop codon, HA tag and the last 15 nucleotides of the I5E coding sequence (not including the stop codon). Therefore, the PCR product contains a HindIII site, I5E coding sequence followed by HA tag fused in frame, a translation termination stop codon next to the HA tag, and an XhoI site. The PCR amplified DNA fragment and the vector, pcDNAI/Amp, are digested with HindIII and XhoI restriction enzymes and ligated. The ligation mixture is transformed into E. coli strain SURE (Strategene Cloning Systems, La Jolla, Calif.) the transformed culture is plated on ampicillin media plates and resistant colonies are selected. Plasmid DNA is isolated from transformants and examined by restriction analysis for the presence of the correct fragment.

For expression of the recombinant I5E, COS cells are transfected with the expression vector by DEAE-DEXTRAN method (J. Sambrook, E. Fritsch, T. Maniatis, Molecular Cloning: A Laboratory Manual, Cold Spring Laboratory Press, (1989)). The expression of the I5E HA fusion protein is detected by radiolabelling and immunoprecipitation method (E. Harlow, D. Lane, Antibodies: A Laboratory Manual, Cold Spring Harbor Laboratory Press, (1988)). Cells are labelled for 8 hours with $^{35}$S-cysteine two days post transfection. Culture media are then collected and cells are lysed with detergent (RIPA buffer (150 mM NaCl, 1% NP-40, 0.1% SDS, 1% NP-40, 0.5% DOC, 50 mM Tris, pH 7.5). (Wilson, I. et al., Id. 37:767 (1984)). Both cell lysate and culture media are precipitated with a HA specific monoclonal antibody. Proteins precipitated are analyzed on 15% SDS-PAGE gels.

8. DEPOSIT OF MICROORGANISMS

The following microorganism was deposited with the American Type Culture Collection (ATCC), 10801 University Boulevard, Manassas, Va. 20110-2209 on Apr. 18, 1997 in compliance with the Budapest Treaty on the International Recognition of the Deposit of Microorganisms, and was assigned the indicated accession number:

| Microorganism | ATCC Accession No. |
| --- | --- |
| e. coli DH10B Ep 065B | 98414 |

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

What is claimed is:

1. An isolated nucleic acid molecule comprising a nucleotide sequence which encodes a polypeptide comprising the amino acid sequence of SEQ ID NO. 2.

2. The isolated nucleic acid molecule of claim 1, wherein said nucleic acid molecule comprises the nucleotide sequence of SEQ ID NO. 1.

3. The isolated nucleic acid molecule of claim 1, wherein said nucleic acid molecule is the nucleic acid insert in ATCC deposit 98414.

4. The isolated nucleic acid molecule of claim 2, wherein said nucleic acid molecule is the coding sequence of the nucleic acid insert contained in ATCC deposit 98414.

5. A vector comprising the isolated nucleic acid molecule of claim 1.

6. A vector comprising the isolated nucleic acid molecule of claim 2.

7. A host cell genetically engineered to contain the nucleic acid molecule of claim 1.

8. A host cell genetically engineered to contain the nucleic acid molecule of claim 2.

9. A host cell genetically engineered to contain the vector of claim 5.

10. A host cell line genetically engineered to contain the vector of claim 6.

11. A host cell genetically engineered to contain the nucleic acid molecule of claim 1, 2, 3, or 4 in operative association with a nucleotide regulatory sequence that controls expression of the nucleic acid molecule in the host cell.

12. An isolated nucleic acid molecule comprising an allelic variant of a nucleotide sequence which encodes a polypeptide comprising the amino acid sequence of SEQ ID NO. 2, wherein said allelic variant hybridizes to the complement of SEQ ID NO:1 under stringent conditions comprising hybridization in 0.5M NaHPO$_4$, 7% SDS, 1 mM EDTA at 65° C., and washing in 0.1× SSC/0.1% SDS at 68° C.

13. A vector comprising the nucleic acid molecule of claim 12.

14. A host cell genetically engineered to contain the nucleic acid molecule of claim 12.

15. A host cell genetically engineered to contain the vector of claim 13.

16. A host cell genetically engineered to contain the nucleic acid molecule of claim 12 in operative association with a nucleotide regulatory sequence that controls expression of the nucleic acid molecule in the host cell.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:

( A ) LENGTH: 4052 base pairs ( B ) TYPE: nucleic acid
( C ) STRANDEDNESS: single
( D ) TOPOLOGY: linear ( i i ) MOLECULE TYPE: DNA ( i x ) FEATURE:
( A ) NAME/KEY: Coding Sequence
( B ) LOCATION: 45...1196
( D ) OTHER INFORMATION:

( x i ) SEQUENCE DESCRIPTION: SEQ ID NO:1:

```
AGCCGCAGAG  CGCACAGAAA  GGAGGCGCCG  AGACAGACAT  CACC ATG GCA GCC CAG        56
                                                     Met Ala Ala Gln
                                                      1

AAT GGA AAC ACC AGT TTC ACA CCC AAC TTT AAT CCA CCC CAA GAC CAT            104
Asn Gly Asn Thr Ser Phe Thr Pro Asn Phe Asn Pro Pro Gln Asp His
 5              10                  15                  20

GCC TCC TCC CTC TCC TTT AAC TTC AGT TAT GGT GAT TAT GAC CTC CCT            152
Ala Ser Ser Leu Ser Phe Asn Phe Ser Tyr Gly Asp Tyr Asp Leu Pro
                 25                  30                  35

ATG GAT GAG GAT GAG GAC ATG ACC AAG ACC CGG ACC TTC TTC GCA GCC            200
Met Asp Glu Asp Glu Asp Met Thr Lys Thr Arg Thr Phe Phe Ala Ala
             40                  45                  50

AAG ATC GTC ATT GGC ATT GCA CTG GCA GGC ATC ATG CTG GTC TGC GGC            248
Lys Ile Val Ile Gly Ile Ala Leu Ala Gly Ile Met Leu Val Cys Gly
         55                  60                  65

ATC GGT AAC TTT GTC TTT ATC GCT GCC CTC ACC CGC TAT AAG AAG TTG            296
Ile Gly Asn Phe Val Phe Ile Ala Ala Leu Thr Arg Tyr Lys Lys Leu
     70                  75                  80

CGC AAC CTC ACC AAT CTG CTC ATT GCC AAC CTG GCC ATC TCC GAC TTC            344
Arg Asn Leu Thr Asn Leu Leu Ile Ala Asn Leu Ala Ile Ser Asp Phe
85                  90                  95                 100

CTG GTG GCC ATC ATC TGC TGC CCC TTC GAG ATG GAC TAC TAC GTG GTA            392
Leu Val Ala Ile Ile Cys Cys Pro Phe Glu Met Asp Tyr Tyr Val Val
                105                 110                 115

CGG CAG CTC TCC TGG GAG CAT GGC CAC GTG CTC TGT GCC TCC GTC AAC            440
Arg Gln Leu Ser Trp Glu His Gly His Val Leu Cys Ala Ser Val Asn
            120                 125                 130

TAC CTG CGC ACC GTC TCC CTC TAC GTC TCC ACC AAT GCC TTG CTG GCC            488
Tyr Leu Arg Thr Val Ser Leu Tyr Val Ser Thr Asn Ala Leu Leu Ala
        135                 140                 145

ATT GCC ATT GAC AGA TAT CTC GCC ATC GTT CAC CCC TTG AAA CCA CGG            536
Ile Ala Ile Asp Arg Tyr Leu Ala Ile Val His Pro Leu Lys Pro Arg
    150                 155                 160

ATG AAT TAT CAA ACG GCC TCC TTC CTG ATC GCC TTG GTC TGG ATG GTG            584
Met Asn Tyr Gln Thr Ala Ser Phe Leu Ile Ala Leu Val Trp Met Val
165                 170                 175                 180

TCC ATT CTC ATT GCC ATC CCA TCG GCT TAC TTT GCA ACA GAA ACC GTC            632
Ser Ile Leu Ile Ala Ile Pro Ser Ala Tyr Phe Ala Thr Glu Thr Val
                185                 190                 195

CTC TTT ATT GTC AAG AGC CAG GAG AAG ATC TTC TGT GGC CAG ATC TGG            680
Leu Phe Ile Val Lys Ser Gln Glu Lys Ile Phe Cys Gly Gln Ile Trp
            200                 205                 210

CCT GTG GAT CAG CAG CTC TAC TAC AAG TCC TAC TTC CTC TTC ATC TTT            728
Pro Val Asp Gln Gln Leu Tyr Tyr Lys Ser Tyr Phe Leu Phe Ile Phe
        215                 220                 225

GGT GTC GAG TTC GTG GGC CCT GTG GTC ACC ATG ACC CTG TGC TAT GCC            776
Gly Val Glu Phe Val Gly Pro Val Val Thr Met Thr Leu Cys Tyr Ala
    230                 235                 240

AGG ATC TCC CGG GAG CTC TGG TTC AAG GCA GTC CCT GGG TTC CAG ACG            824
Arg Ile Ser Arg Glu Leu Trp Phe Lys Ala Val Pro Gly Phe Gln Thr
245                 250                 255                 260
```

```
GAG CAG ATT CGC AAG CGG CTG CGC TGC CGC AGG AAG ACG GTC CTG GTG          872
Glu Gln Ile Arg Lys Arg Leu Arg Cys Arg Arg Lys Thr Val Leu Val
            265                 270                 275

CTC ATG TGC ATT CTC ACG GCC TAT GTG CTG TGC TGG GCA CCC TTC TAC          920
Leu Met Cys Ile Leu Thr Ala Tyr Val Leu Cys Trp Ala Pro Phe Tyr
            280                 285                 290

GGT TTC ACC ATC GTT CGT GAC TTC TTC CCC ACT GTG TTC GTG AAG GAA          968
Gly Phe Thr Ile Val Arg Asp Phe Phe Pro Thr Val Phe Val Lys Glu
            295                 300                 305

AAG CAC TAC CTC ACT GCC TTC TAC GTG GTC GAG TGC ATC GCC ATG AGC         1016
Lys His Tyr Leu Thr Ala Phe Tyr Val Val Glu Cys Ile Ala Met Ser
        310                 315                 320

AAC AGC ATG ATC AAC ACC GTG TGC TTC GTG ACG GTC AAG AAC AAC ACC         1064
Asn Ser Met Ile Asn Thr Val Cys Phe Val Thr Val Lys Asn Asn Thr
325                 330                 335                 340

ATG AAG TAC TTC AAG AAG ATG ATG CTG CTG CAC TGG CGT CCC TCC CAG         1112
Met Lys Tyr Phe Lys Lys Met Met Leu Leu His Trp Arg Pro Ser Gln
            345                 350                 355

CGG GGG AGC AAG TCC AGT GCT GAC CTT GAC CTC AGA ACC AAC GGG GTG         1160
Arg Gly Ser Lys Ser Ser Ala Asp Leu Asp Leu Arg Thr Asn Gly Val
            360                 365                 370

CCC ACC ACA GAA GAA GTG GAC TGT ATC AGG CTG AAG TGACCCACTG GTGTCA       1212
Pro Thr Thr Glu Glu Val Asp Cys Ile Arg Leu Lys
            375                 380

CACAATTGAA AACCCCAGTC CAGTACTCAG AGCATCACCC ACCATCAACC AAGTTCATAG       1272
GCTGCATGGG AAATGACATC TGTGTTCATG CCTCCCCCGT GCCCTCAAGA AGCCGAATGC       1332
TGCAAAGTCG TAACATACAA TGAGACTAGA CATGAACCAA ATCAGCTGAC ATTTACTGAT       1392
ATCCGCTCGA CACCTACTGT GTCCACAATC CCCACAAGGA GATTAGACAC AAGGAGCAGC       1452
AACTGACATG GACTGAACAT GTACTGTGTG CAAACCACAC CAATGAGATT AGACGGGGAC       1512
AGCAGGAGCT GACATTTACT CTTCACCTAC TGTAATCAAA AACACTTGAT TTGATTACAA       1572
TCAAAAACAT ATAAAAAACA TAACAAAGTA GCAGAAGCTA TTGGAGTTTC CAAGCTATCT       1632
CCAGATATAT AGATAGTTCA CCCTCCATCT TCCCTAATTC TGTATCTTAC CAGTGCAGGA       1692
ATATCAAAAG CTATAGGCC AGGCATGATG GCTCATGCCT GTAATCCCAG CACTTGGGGA        1752
GGCTGAGGCA CGTGGATCAC TTGAGGTCAG GAGTTCAACC CAGGCTGGCC AACATGGTGA       1812
AACCCTGTCT CTACTAAAAA TACAAAATTA GCTAGGCGTG GTGGCGGGCG CCTGTAATCC       1872
CAGTTACTCA GGAGGCTGAA GCAGGAGAAT AGCTTGAACC TGGGAGTTGG AGTTTGCAGT       1932
GAGCTGAGAT TGCTCCACTG CACTCCAGCC TGAGTGACAG AGTGAGACTC TGTCTCAGGA       1992
AAAAAACAAA CAAACAAACA ACAAAACAAC AACAACAACA ACAACAACCA ACGGCTATAG       2052
AAGAAGACTC TTCGACACAA TGGAAATGTA ACGATAAGTT TGTCAGTGCG TGGTTTACAG       2112
CATCATGGGA GGTGCGTTAC AGCCATCATA CTGAACTTTC CCACCCACCT CCTACTGCCT       2172
CCCAGGGCAT TCTCTAGGAT TTTGGCTTCA AGAAAAAAAA AATTCTTATA GTCAGCCCAG       2232
CCTTATGTGG TTATCCACAA TGGTGTAATT TCAAAGGAAA GAACCTAAAA ATCACTTTCC       2292
CACTGATGCT TGAAAGCTTA TCATTTTATT TGGGTGGAGA TGGGTAATCC TGAGGTGTCA       2352
ATTTTTGCCT CCTCAGTGCA AAGGATTTCA GTGGCTCTGG GGTCAGGGGG AAAGAGGACA       2412
GAGAAAAAAG TGGAGGTTGC CACTGGCAAT GAACATAATC TCTGTGGGCA TTTTGCTAAG       2472
GACTGGACCA CTTTCTAGAA CACTCCCTCT TTTACAAAAG GAACTCTACC TAGAATCCAA       2532
AGACCTGGGT TCAGGTCCTA ACTCTAAGAC TCAAGTCCTA AATTCATGAT GTTTTCTCTC       2592
TGTGTCTCAG TTTTGCTTTA ATGAAATGGC GATGATGAAA ATATCTGCTC TTCATACCTT       2652
```

-continued

```
GCAAGACTGT  TGGGAGAGCC  CATTGAGGCC  ATGGTTTGTG  AATGTGCTTT  TCAACTGTGC  2712
ACACGATAAG  AATGGAGAAG  TGATATTGAA  CAGTTTATTT  GGAGGGAGTT  TATTTGGAAA  2772
CCCCATCCAC  TGTGATTTAT  TAGAGAAATA  CCCACACTTT  TTCATCCCTG  TTCTTTGGAT  2832
GAAAGACTCC  TGAAGACTTC  ACAGTGTACC  TTGTCTACAG  TGGGCCAAAA  AGGGATCCCT  2892
GTTCTTGGTT  ATAATCTGGG  AAATTTAACC  TCAGATTCTC  AGTGACCCCA  AGACTCTCAG  2952
CATCCCTGCG  GTCTTAGAAG  TGTTGACAGT  CTTCCCTGCA  TGTTGCAAAA  TAGCACCCTA  3012
GTGCTGCATA  AATATCACTT  CTGAATCTGT  TTGTATTATT  ATACATTTGT  GGTAACTGTA  3072
GGTACACGTC  TTCATTTCTT  CTTGATTCAT  TTTGATGTGG  TAGCTATGCA  AATGGTACCT  3132
GGTTTGGGAC  TGACCCATCC  ATATTTGACC  AATTCCTAAT  TTTTTATAGA  CAAGGAATTA  3192
ATTGTTTGCT  TGTTTGATTG  TTTCTATTAT  TTGTTGATTT  GTTTCTCTGA  CTGAAGTTTC  3252
AACCAATGTT  TCTTTCTATC  ACCACCCAGC  AGACTCACCT  TCAGCCCAAT  CATTGTACTC  3312
TCAGAAAATG  CAGGCCGGCA  TGGTGGCTCA  CATCTGTAAT  CCCAGCACTT  CGGGAGGCCA  3372
AGATGGGCAG  ATCACCTGAG  GTCAGGAGTT  CAAGACCAGC  CTGGCCAACA  TGGCAAAACC  3432
CCATCTCTAG  AAAAATACAG  AAATTAGCTG  GCGTGGTGGC  ACATGCCTGT  GGTCCCAGCT  3492
CCTCAGGAGG  CTGAGGCATG  AGAATTGCTT  GAACCCCAGA  GGCAGAGGTT  GCAGTGAATT  3552
GAGATCGCAC  CACTGCACTC  CAGCCTGGGT  GATAGAGCAA  GATTCCATCT  CAAAAGGAAA  3612
ATAAAGAAA   ATGCAAACAC  ACTATAATAT  TAGCCTAAGC  AAAACTGTTA  ATTCTGATTT  3672
ACAAAAATTC  TTACTTGCTT  GGCTTTGAAA  TGCATTGTGT  AATAATGCAT  TTCAAAGCCA  3732
AGCAAGTAAC  AATTTTAGGT  TATGTACATT  TCTATAAATA  TAATAATTGT  ATTTTTATTT  3792
ATTATTCTAT  CCTGGCTCTT  AGCCGAATCA  GGAGATTCTT  TAGGAATGGA  CCATGTACCA  3852
GTCAAGTCTG  TCAGCAGGAT  TCATCACCCT  GTTCCTTTTT  GTCCTAGAAT  ATACCAACTT  3912
CCTTTCATTG  AAATTTAACT  GAAAAAACTT  TTGTAAATAT  CAGTGTGTAT  TTGTGATTTT  3972
CCAGTGATTA  AAGTGTGATG  TTGTTATCCA  ATTAAATAAT  TAACATGTGG  AATTTAAAAA  4032
AAAAAAAAAA  GGGCGGCCGC                                                  4052
```

( 2 ) INFORMATION FOR SEQ ID NO:2:

( i ) SEQUENCE CHARACTERISTICS:
        ( A ) LENGTH: 384 amino acids
        ( B ) TYPE: amino acid
        ( C ) STRANDEDNESS:
        ( D ) TOPOLOGY: unknown ( i i ) MOLECULE TYPE: protein ( x i ) SEQUENCE DESCRIPTION: SEQ ID NO:2:

```
Met  Ala  Ala  Gln  Asn  Gly  Asn  Thr  Ser  Phe  Thr  Pro  Asn  Phe  Asn  Pro
 1                 5                     10                      15
Pro  Gln  Asp  His  Ala  Ser  Ser  Leu  Ser  Phe  Asn  Phe  Ser  Tyr  Gly  Asp
                20                     25                      30
Tyr  Asp  Leu  Pro  Met  Asp  Glu  Asp  Glu  Asp  Met  Thr  Lys  Thr  Arg  Thr
                35                     40                      45
Phe  Phe  Ala  Ala  Lys  Ile  Val  Ile  Gly  Ile  Ala  Leu  Ala  Gly  Ile  Met
           50                     55                      60
Leu  Val  Cys  Gly  Ile  Gly  Asn  Phe  Val  Phe  Ile  Ala  Ala  Leu  Thr  Arg
65                      70                     75                      80
Tyr  Lys  Lys  Leu  Arg  Asn  Leu  Thr  Asn  Leu  Leu  Ile  Ala  Asn  Leu  Ala
                85                     90                      95
```

| | | | | | | | | | | | | | | |
|---|---|---|---|---|---|---|---|---|---|---|---|---|---|---|
| Ile | Ser | Asp | Phe 100 | Leu | Val | Ala | Ile 105 | Ile | Cys | Cys | Pro | Phe 110 | Glu | Met | Asp |
| Tyr | Tyr | Val 115 | Val | Arg | Gln | Leu | Ser 120 | Trp | Glu | His | Gly | His 125 | Val | Leu | Cys |
| Ala | Ser | Val 130 | Asn | Tyr | Leu | Arg | Thr 135 | Val | Ser | Leu | Tyr | Val 140 | Ser | Thr | Asn |
| Ala 145 | Leu | Leu | Ala | Ile | Ala 150 | Ile | Asp | Arg | Tyr | Leu 155 | Ala | Ile | Val | His | Pro 160 |
| Leu | Lys | Pro | Arg | Met 165 | Asn | Tyr | Gln | Thr | Ala 170 | Ser | Phe | Leu | Ile | Ala 175 | Leu |
| Val | Trp | Met | Val 180 | Ser | Ile | Leu | Ile | Ala 185 | Ile | Pro | Ser | Ala | Tyr 190 | Phe | Ala |
| Thr | Glu | Thr 195 | Val | Leu | Phe | Ile | Val 200 | Lys | Ser | Gln | Glu | Lys 205 | Ile | Phe | Cys |
| Gly | Gln 210 | Ile | Trp | Pro | Val | Asp 215 | Gln | Gln | Leu | Tyr | Tyr 220 | Lys | Ser | Tyr | Phe |
| Leu 225 | Phe | Ile | Phe | Gly | Val 230 | Glu | Phe | Val | Gly | Pro 235 | Val | Val | Thr | Met | Thr 240 |
| Leu | Cys | Tyr | Ala | Arg 245 | Ile | Ser | Arg | Glu | Leu 250 | Trp | Phe | Lys | Ala | Val 255 | Pro |
| Gly | Phe | Gln | Thr 260 | Glu | Gln | Ile | Arg | Lys 265 | Arg | Leu | Arg | Cys | Arg 270 | Arg | Lys |
| Thr | Val | Leu 275 | Val | Leu | Met | Cys | Ile 280 | Leu | Thr | Ala | Tyr | Val 285 | Leu | Cys | Trp |
| Ala | Pro 290 | Phe | Tyr | Gly | Phe | Thr 295 | Ile | Val | Arg | Asp | Phe 300 | Phe | Pro | Thr | Val |
| Phe 305 | Val | Lys | Glu | Lys | His 310 | Tyr | Leu | Thr | Ala | Phe 315 | Tyr | Val | Val | Glu | Cys 320 |
| Ile | Ala | Met | Ser | Asn 325 | Ser | Met | Ile | Asn | Thr 330 | Val | Cys | Phe | Val | Thr 335 | Val |
| Lys | Asn | Asn | Thr 340 | Met | Lys | Tyr | Phe | Lys 345 | Lys | Met | Met | Leu | Leu 350 | His | Trp |
| Arg | Pro | Ser 355 | Gln | Arg | Gly | Ser | Lys 360 | Ser | Ser | Ala | Asp | Leu 365 | Asp | Leu | Arg |
| Thr | Asn 370 | Gly | Val | Pro | Thr | Thr 375 | Glu | Glu | Val | Asp | Cys 380 | Ile | Arg | Leu | Lys |

( 2 ) INFORMATION FOR SEQ ID NO:3:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:3:

TGCTGCTTAA ACCTGGGTCG G        21

( 2 ) INFORMATION FOR SEQ ID NO:4:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:4:

GGTGTGTGAT TTACTGAGTA CCG                                                                23